US006555228B2

(12) United States Patent
Guritza

(10) Patent No.: US 6,555,228 B2
(45) Date of Patent: Apr. 29, 2003

(54) BIO-SUPPORTIVE MEDIUM, AND METHODS OF MAKING AND USING THE SAME

(76) Inventor: Dennis A. Guritza, 17727 Lost Trail, Chagrin Falls, OH (US) 44023

( * ) Notice: Subject to any disclaimer, the term of this patent is extended or adjusted under 35 U.S.C. 154(b) by 0 days.

(21) Appl. No.: 09/776,198

(22) Filed: Feb. 2, 2001

(65) Prior Publication Data

US 2002/0045057 A1 Apr. 18, 2002

Related U.S. Application Data

(60) Provisional application No. 60/240,792, filed on Oct. 16, 2000.

(51) Int. Cl.$^7$ .............................. B32B 27/38; B32B 9/04; A01N 27/00
(52) U.S. Cl. ..................... 428/414; 428/413; 428/423.1; 428/447; 428/457; 428/480; 428/523; 428/537.1; 428/411.1; 106/14.05; 523/122; 424/78.09
(58) Field of Search .............................. 428/413, 423.1, 428/447, 457, 474.4, 480, 492, 500, 523, 537.4, 537.1, 414; 523/122; 106/14.05; 424/78.09

(56) References Cited

U.S. PATENT DOCUMENTS

| | | | | | |
|---|---|---|---|---|---|
| 3,979,354 | A | * | 9/1976 | Dyckman et al. | 260/37 EP |
| 4,177,302 | A | | 12/1979 | Weiss | |
| 4,197,233 | A | | 4/1980 | Marshall | |
| 4,221,839 | A | | 9/1980 | de Graff | |
| 4,260,700 | A | | 4/1981 | Cassutt et al. | |
| 4,323,599 | A | | 4/1982 | Marshall | |
| 4,428,989 | A | | 1/1984 | Marshall | |
| 4,500,339 | A | * | 2/1985 | Young et al. | 106/15.05 |
| 4,521,475 | A | | 6/1985 | Riccio et al. | |
| 4,561,981 | A | | 12/1985 | Characklis | |
| 4,576,838 | A | | 3/1986 | Rosen et al. | |
| 4,593,055 | A | | 6/1986 | Gitlitz et al. | |
| 4,996,261 | A | | 2/1991 | Lebovitz et al. | |
| 5,035,759 | A | | 7/1991 | Andoe | |
| 5,116,407 | A | | 5/1992 | Hunter et al. | |
| 5,246,489 | A | | 9/1993 | Farmer et al. | |
| 5,284,587 | A | | 2/1994 | Wong et al. | 210/606 |
| 5,284,682 | A | | 2/1994 | Martin | |
| 5,336,304 | A | | 8/1994 | Andoe | |
| 5,354,603 | A | | 10/1994 | Errede et al. | 428/240 |
| 5,403,390 | A | | 4/1995 | Spera et al. | |
| 5,571,312 | A | | 11/1996 | Andoe | |
| 5,693,527 | A | | 12/1997 | Imamura | 435/262 |
| 5,760,103 | A | | 6/1998 | Wentzel | |
| 5,773,508 | A | * | 6/1998 | Tendo et al. | 524/547 |
| 5,814,172 | A | | 9/1998 | Cox et al. | |
| 5,861,435 | A | * | 1/1999 | Yokoi et al. | 424/78.09 |
| 5,883,156 | A | * | 3/1999 | Fukuda et al. | 424/78.09 |
| 5,885,029 | A | * | 3/1999 | Kotani et al. | 405/211 |
| 6,017,334 | A | * | 1/2000 | Rawls | 604/265 |
| 2001/0027225 | A1 | * | 10/2001 | Downie | 523/124 |

OTHER PUBLICATIONS

PCT/US01/32286; PCT International Search Report mailed Mar. 22, 2002.
"Marine Fouling and Its Prevention" by Woods Hole Oceanographic Institution (1957).
"Evaluation of Protective Coating Systems for Buoys", R.J. Dick, et al, for Department of Transportation, U.S. Coast Guard, Federal Document No. ADA054279, May 31, 1977.
"The Biological Importance of Copper in Oceans and Estuaries", Lewis, A.G. and Cave, W.R., Oceanography and Marine Biol. Ann. Rev, 1982,20,471–695 (Aberdeen Univ. Press).
"Analysis of Buoy Coating Specimens Exposed in Seawater at Daytona Beach, Florida", R.J. Dick, et al, for Department of Transportation, U.S. Coast Guard, Federal Document No. ADA011274, Mar. 21, 1975.
"Action of Antifouling Paints, Use of Glycine as Accelerated Test of Availability of Toxic", Ketchum, Bostwick H., Ind. & Eng. Chem., 40, p. 249 (1948).
"Action of Antifouling Paints, Solubility and Rate of Solution of Cuprous Oxide in Sea Water", Ferry, J.D. and Carritt, D.E., Ind. & Eng Chem., 38, 612–17, (1946).
"Action of Antifouling Paints, Solubilities of Antifouling Toxics in Sea Water", Ferry, J.D. and Riley, G.A., Ind. & Eng. Chem., 38, 699–701 (1946).
Kirk–Othmer Encyclopedia of Chemical Technology, vol. 6, p. 445–454, 3$^{rd}$ Ed., (1979); Coatings, Marine.
"Standard Test Method for Subjecting Marine Antifouling Coating to Bio–fouling and Fluid Shear Forces in Natural Seawater", ASTM method D4939–89, vol. 06.02, (1995), (ASTM at 1916 Race Street, Philadelphia, PA 19103–1187).

* cited by examiner

Primary Examiner—Robert Dawson
Assistant Examiner—Michael J Feely
(74) Attorney, Agent, or Firm—Hahn Loeser + Parks LLP; Stephen L. Grant

(57) ABSTRACT

The instant invention is a bio-supportive medium comprising a degradable material, at least one nutritional source, and at least one bio-limiting agent dispersed in the biodegradable material. The nutritional source is present in the degradable material or an additive to the degradable material. The components of the bio-supportive medium are provided in quantities, such that the bio-supportive medium is capable of supporting formation of a biomass having a specific consortium of organisms, substantially at equilibrium within its environment or host habitat. While maintaining the biomass, the bio-limiting agent also provides the bio-supportive medium to limit the amount and type of species present in the biomass. The instant invention provides a unique bio-mimicking and environmentally-friendly way to control fouling of materials exposed to marine and aquatic environments.

38 Claims, No Drawings

BIO-SUPPORTIVE MEDIUM, AND METHODS OF MAKING AND USING THE SAME

CROSS REFERENCE TO RELATED APPLICATIONS

This application claims priority from provisional application Serial No. 60/240,792 filed Oct. 16, 2000, the entire disclosure of which is hereby incorporated by reference.

FIELD OF THE INVENTION

This invention relates to a stenoprophiluric media and methods of making and using the same. More specifically, the invention relates to a stenoprophiluric media which comprises at least one bio-limiting agent. The stenoprophiliuric media limits the number and kinds of organisms attached to or associated with the media. The stenoprophiluric media provides for the formation of a micro-habitat(s).

BACKGROUND OF THE INVENTION

Chemical corrosion, such as hydrolysis and biological corrosion and bio-fouling are naturally occurring processes which have been both a benefit and a problem for man for centuries. Fortunately, microbes breakdown organic matter and decompose everything from banana peels to large mammals. Bio-deterioration, however, may also decompose our national treasures and monuments. In aquatic environments, microbes also may attack and break down substrates and inorganic materials using them as sources of food and necessary critical nutrients. Bio-fouling occurs when creatures excrete enzymes which can for example digest such things as bridges and concrete waterways. Sometimes this may occur in concert with or dependent from simple chemical corrosion from sea water or other environmental effects, such as hydrolysis. At the same time, bio-fouling is also characterized by attachment of organisms, both plant or animal, to structures and hulls and building biomass which may block flow in pipes, (such as the organisms which blocked water cooling pipies in the Chernobyl nuclear power plant disaster) or create tremendous weight imbalances on deep water structures.

For 4000 years, man has tried various means to manage and reduce the degradative effects of organism attachment (fouling), corrosion and consumption of man-made structures and vessels in marine, freshwater, and hydrophytic aquatic environments. Early Egyptians clad their vessels with copper. Centuries later mercury compounds were smeared on boats and nets to extend their useful life. In the energy limited days of the 1970's, extremely effective toxins were used to eliminate any fouling. Fouling can increase drag on ships and raise operating cost by as much as 40%.

Over the last 30 years, international concern for the environment has placed all previous toxic release methods of controlling corrosion and fouling in very bad light. These toxic coatings, while eliminating one problem, create another one, e.g., the introduction of toxins to waterways. Toxins, used to prevent bio-fouling and corrosion, have part per trillion toxicity and have eradicated life forms in harbors and estuaries in many internationally navigable ports in industrial countries. Their toxicity has resulted in outright bans of their use.

Attempts have been made to reduce and moderate the toxicity concentration in coatings. Simple anti-corrosive coatings, especially those without toxins, have very short service lives. They are quickly attacked and are often consumed by organisms and natural corrosion. Thus only toxic repellents were developed.

Two methods of delivering toxins in coating systems have prevailed; 1) soluble coatings and 2) insoluble coatings. These coatings have lead to irregular and uncontrolled discharge of toxins. Thus, concern for the environment has perceptively stymied all known toxic approaches to provide safe and cost effective management of man-made surfaces in both aquatic and hydrophytic environments. Further, the assumption for decades has been that all biological growth on a substrate is undesirable because it inevitably leads to succession of species to the undesired types of organisms, like barnacles in salt water and zebra mussels in freshwater.

In insoluble coatings, the leaching of toxins from the coating is the rate control mechanism. This system has very limited duration and efficacy of service life. In soluble coatings, the coating dissolves in water with the uncontrolled release of contained toxins being accelerated by movement of the vessel. Over 90% of the toxin of the soluble coating is released to the environment which affects non-targeted biological species. This release usually leads to negative ecological effects. To date the assumption has been that anti-fouling and anti-corrosion control can only be achieved through toxic means to the exclusion of any and all biomass.

While chemical corrosion of metal, concrete, and wood structures by the environment or habitat is well understood, it must also be realized that biodegradation is a mechanism of gaining access to or managing the release of nutrients of a substance as a food source for growth and reproduction of organisms. Available nutrients, both in terms of presence and availability is a significant limiting criteria in the success or failure of any organism. For instance, copper is an important essential nutrient, yet copper carbonate is insoluble in most aquatic and biological systems. Therefore, while copper is present, it is unavailable for use.

The combination of organism(s), nutrient(s), and agents in a given environment form a sub-habitat. A sub-habitat, often defined as a micro-habitat, may be created when these conditions create a unique set of properties for a sustained period of time. A specific example of natural micro-habitats is the slime found on fish. The slime prevents infections and controls the interface between the organism (fish) and the environment. In the case of mammals, cows maintain a five bacteria consort of microbial slime in their digestive system which facilitates the digestion of cellulose. Unique "micro-habitats" may be formed where functionality of a unique set of nutrient, bio-limiting agents, and relationships provide conditions that support the organism or consort of organisms in a sustained manner which are different than the host habitat. Micro-habitats often develop the ability to limit ingress and egress of nutrients, water, waste, and biological incursions by other organisms.

Understanding the field of biodegradation has been clouded for years due to the lack of recognition of the differences and influences created by the host habitat. Both the patent and popular literature discuss the biodegradation processes, critical parameters influencing the rate of degradation and outcomes of biodegradation, as well as information on how to influence or direct those outcomes. Often, the fact that a host habitat can greatly influence the bio-degradative system being studied, and may lead an unaware reader to incorrect conclusions, is not clearly provided. Biodegradation in aqueous environments is much different than in water-limited land based environments. Water is omnipresent, nutrients including oxygen are in greater supply, and the water media provides a greater opportunity for microbial presence. "Biomimicry" was made topical in 1997 with the publication of a book by Jannine M. Benyus with a subtitle "Innovation Inspired by Nature". The aim of the book is to focus attention on natural systems which solve complex problems. Many examples and novel applications have been studied which relate mimicry to corrosion, invasion, fouling, and deterioration. Pine trees when physically injured by storm or other incident exude a sap like substance which hardens, preventing loss of water, and keeping insects from invading the tree. The sap degrades without leaving a trace after sufficient tree growth and recovery over several months. In another example, a cow creates a slime layer in its intestine to protect it (the intestinal wall) from many complex and highly corrosive and degradative reactions required to decompose cellulose for digestion and extraction of the nutrients. This matrix has been described as a "slime city" where a biomass related to five distinctly different bacteria form a polysaccharide complex system which forms channels and pathways. The members of the consortium are very diverse in that one organism tolerates methane (a product of the decomposition) while another organism (close to the intestinal wall) can not survive in the presence of methane. Yet in this very thin layer these organisms are at equilibrium symbiotically and for the benefit of the host. In the ocean, in very diverse shallow marine habitats a micro-habitat of a colonial organism called a protocist can assist in the creation of an elaborate network with very unique functionality identified as labyrinthulata. Each of these systems have unique functional properties while sharing a number of commonalities which, when managed appropriately, can mimic natural and non-harmful solutions like corrosion, fouling, and deterioration.

A need exists for a method and composition which limits the biomass without being anti-biotic, i.e., killing organism of the biomass. A need exists for a pro-biotic system which promotes selective growth of a biomass.

SUMMARY OF THE INVENTION

This invention relates to an article comprising a stenoprophiluric media having at least one bio-limiting agent. When the stenoprophiluric media is placed in an aqueous environment, a biofilm or consortium of organisms forms on the stenoprophiluric media. The type of biofilm or consortium which forms is different from that which would form in the absence of the biolimiting agent. The stenoprophiluric media is biodegradable and is consumed by the organisms of the biofilm or consortium. The stenoprophiluric media may be used as a pedigreed media to provide a biological growth medium. A pedigree media is a media whose composition is consistent and whose effects or ramifications are known. The stenoprophiluric media may also be used to form a barrier to corrosion (both chemical and biological), consumption, deterioration and/or invasion.

The bio-degradation rate of the stenoprophiluric media provides for exposure of the bio-limiting agent. This relationship provides for a managed release or managed availability of the bio-limiting agent, which creates a new set of ecological conditions. These conditions can maintain a micro-habitat, e.g., a limited consort of species, often in the form of a slime. These consorts can utilize allelopathic means to further protect their position, and deter invasion and predation of higher organisms. Another advantage of the biomass is that the production of allelopathic chemicals prevents attachment of higher animals. The biomass also provides protection of the substrate from corrosion.

The invention also relates to the stenoprophiluric media and methods of using the media. The present invention can be used as a biological barrier to unwanted organisms, such as animals and plants, by limiting the level of succession to lower order organisms, such as microbes. These microbes may further protect their position or attachment space by producing allelochemicals that either kill or repel competing or predatory organisms. The media and its supporting materials may also serve as an insulation for the substrate. The media may be formed with one or more sub-layers between it and the substrate to prevent access of the biomass to certain elements or compounds in the substrate which may alter the biomass with the presence or absence of nutrients or agents. The invention could be used as a coating on a vessel to prevent fouling. The invention could be used on structures in all forms of aquatic environments. The invention may also be used to manufacture specific allelochemicals, such as drugs or pharmaceuticals. The invention also relates to a method of preparing a bio-limiting ecological substrate useful as a means for producing allelochemicals, comprising the steps of providing a stenoprophiluric media, and exposing the media to the environment, wherein the media is formulated to provide a biomass that produces the desired uniquely targeted allelochemicals. The stenoprophiluric media provides a durable support layer for a biomass. The biomass may be selected to produce specific allelochemicals that have pharmaceutical or bio-active properties. The physical media and its components may be adjusted to select targeted species of organisms. The media could be added to rocks or structures in a habitat to provide new nutrients which are lacking, new agents which can alter the host environment, or provide the media for introduction of desirable species with the aim of habitat restoration.

The media may be used to coat pipes in process streams where both bio-corrosion and fouling as well as with drag can be more readily managed.

Terms and Definitions

Bioavailability—Nutrients and bio-limiting agents must be able to have an effect with the habitat. These materials are biologically available not just present. For example, cuprous oxide would be an available form of copper supply for most ecosystems while copper carbonate is essentially insoluble.

Host habitat—the habitat in which a micro-habitat exists. Marine, brackish, fresh, and hydrophytic water environments are typical examples. A host habitat could also be defined as inside a mammalian animal, a land fill, a closed water system (single pass or re-circulating), a chemical process stream, and a stagnant water holding system, like those used in fire control systems.

Micro-habitat—a small, specialized, and effectively isolated location within the host habitat where a specific combination of habitat elements in the place is occupied by an organism or limited consortium of organisms. A micro-habitat demonstrates bioceonose; a community of organisms whose composition and aspect is determined by the properties of the environment including media and by the relations of the organisms to each other.

Stenoprophilicity—the ability to maintain a micro-habitat through the use of stenoprophiluric media while accounting for or managing secondary environmental parameters to achieve and support maintenance of a micro-habitat. Stenoprophilicity also involves supporting parameters to the substrate or host habitat that facilitates the micro-habitat, i.e., addition or subtraction of available light, respiratory gases such as oxygen, adjustment of pH, adjustment of temperature of the substrate or the host habitat, addition or elimination of host habitat derived essential nutrients.

Stenoprophilurea—A media/polymer, composite, or amalgam which provides surface, nutrition, and bio-limiting activity which facilitates the creation and sustenance of micro-habitats for extended periods of time at equilibrium with its host environment.

DETAILED DESCRIPTION OF THE PREFERRED EMBODIMENTS

As described above, the present invention is directed to a stenoprophiluric media having at least one bio-limiting agent. The media is capable of supporting a biomass. The biomass is composed of organisms found in the macro-habitat. The media is subject to hydrolysis, corrosion and consumption by the biomass. If a biomass grows uncontrolled and progresses through multiple successive steps to higher life forms, the media will only serve to accelerate growth and create an over diverse habitat. The biomass will consume the media and essentially have no long term positive effect. In the present invention, the media limits the biomass resulting in a sub- or individualized micro-habitat. The media with the bio-limiting agent provides the opportunity for the specialized consortium of organism(s) (i.e., biomass) to form. It is understood that alga and bacteria may have "growing seasons" within the host habitat. The stenoprophiluric media would, under those conditions, have its effect during those growing times.

The present invention involves biodegradation or consumption of an stenoprophiluric media by a biomass. The biomass forms a specific consortium of organisms of the same or different species at equilibrium with the environment or host habitat and limits the numbers and kinds of species participating in the micro-habitat. Previously, systems used toxins to kill organisms. The present invention provides a bio-limiting agent which limits the interaction of organism(s).

As described above, the present invention relates to a stenoprophiluric media which contains at least one bio-limiting agent. The stenoprophiluric media acts to provide a new sub-habitat which supports a biomass, which is often described as a biofilm or micro-habitat. The functional activity of the media and bio-limiting agent to support formation of a biomass is defined as Stenoprophilicity.

The biomass may be a biofilm or consortium on the stenoprophiluric media. The biomass is an adjunct consortium on or affixed, or proximal to the media. A common description of the biomass is "slime". This definition includes the secondary metabolites of the organisms in the biomass or consortium. The micro-habitat may be as thin as a single layer of organisms on the surface of the media or a thick layer having a complex series of pathways of extra-metabolic materials. The thicker layer may create "slime cities" of multiple species forming intermediate zones between various parts of the micro-habitat.

Stenoprophiluric Media

The stenoprophiluric media may be classified as a polymer, a composite, or an amalgam. The media is biodegradable and is consumed by the biomass. The media is subject to hydrolysis and corrosion. This degradation is accomplished through hydrolysis, oxidation, inorganic dissolution or biochemical dissolution where organisms create enzymes or metabolic chemicals to "digest" the media. The degradation makes available the biolimiting agent for the biomass. The bio-degradation rate or the rate of media consumption is determined by the number of sites in the molecular level structure of the media where oxidation, hydrolysis, dissolution, or digestion can occur. In most commercial polymers, paints, and coatings, these sites are minimized to prevent the degradation from occurring.

The types of molecules and substances in the media also determine which biomass and what types of organisms are capable of decomposing the media. Nitrogen-rich or carbon-rich materials attract specific organisms. Iron seeking microbes are more attracted to steel than a polymer or matrix which has no iron content. The media and biolimiting agent will determine the consortium attracted to the media surface.

The media may be classified as a composite composed of two or more substances which retain their identity while contributing desirable properties to the end product. The composite may be naturally occurring materials, such as polysaccharides, lipids, and/or proteins or materials referred to as polymers which are typically man-made engineered materials. By adjusting the biological and chemical degradation rate of the media, the media creates a preferential environment which limits or attracts specific organisms able to associate with the media. The media becomes a support (both physically and nutritionally) for limited biological growth and provides an interface which facilitates a selective biomass formation as a micro-habitat in equilibrium with the environment. Due to the depth or thickness of the stenoprophiluric media the micro-habitat is sustained for extended periods of time at equilibrium with the proximal environment or habitat in which it is established as a sub-environment or niche.

The biodegradation of the media is affected by the availability of sites for corrosion, e.g., hydrolysis or consumption by organisms. The sites of attack are typically polar in nature. In the present invention, the media has sites which provide locations for degradation. When the media is based on a polymer, the polymer is usually reacted to have excess polarity. For instance, polymers are prepared by reacting at least di-functional materials. In the present invention, the ratio of the reactants is such that there is an excess of polar reactants. For esters, there could be either an excess of acid or hydroxyl groups. Typically, polymers are prepared using an equivalent ratio of greater than about 1:1. In one embodiment, the polymer is prepared by having from about 0.2 to about 1, or from about 0.3 to about 1.5 or from about 0.5 to about 1 excess equivalents of polar ingredients. For instance, typical polymers are prepared with an equivalents ratio of about 1:1. The polymers of the present invention are prepared with equivalent ratios of about 1:1.1 to about 1:3. For example, a polyester is prepared by reacting a carboxylic acid group with a hydroxy group. A typical polyester is prepared using a ratio of about one carboxylic group for each hydroxyl group. If the polyester is to be used in the stenoprophiluric media then the ratio of carboxylic groups to hydroxyl groups is greater than 1:1.

In one embodiment, the polymers are reacted in an equivalent basis of about 0.35 or about 0.5 to about 0.95, or from about 0.7 to about 0.9 equivalents of component A to component B. It is to be understood that the definition of equivalents for the components is determined by the reactive units. The equivalents for acids or alcohols is determined by the number of acid or alcohol groups in the molecules. It should be noted that the excess component is not limited. In polyesters, either the acid or alcohol may be present in excess. Polymers, involving reaction with amines, could have an excess of amine. Polyurethane polymers may have excess hydroxyl or amine groups from the reactants.

Commercial polymers are not normally biodegradable. These commercial polymers are prepared with no excess polar groups. These polymers may be rendered biodegradable by either altering their production conditions as discussed above or adding excess cross-linking agent. The polymers may also be trated with radiation, such as an electronbeam, to cause the polymer to be biodegradable. Additionally, the polymer may be oxidized using commercial oxidizing agent like peroxides and perchlorates. Finally, the polymers may be altered by adding chain stopping agent to the reaction mixture. Chain stopping agents are known to those in the art and include mercaptans, monofunctional materials like alcohols, monoamines, etc.

Cross-Linking Agents

In another embodiment, the polymers are prepared using a cross-linking agent. The cross-linking agents include certain compounds and chemical additives which facilitate formation of linkages at preferred locations or combinations of molecules and/or chains of molecules which provide preferred physical and chemical properties. Examples of cross-linkers include; mercaptans, acids, anhydrides, epoxide functional resins, organotins, amines, alcohols, phenols, water, cycloaliphatic amines, aromatic amines, ketimines, carboxylic acids, and super acids ($F_3CSO_3H$) ($HSbF_6$) ($HPF_6$). These materials are described herein. The cross-linking agents are discussed below and include polyhydroxy compounds and resins, amines, including monoamines and polyamines, etc.

The amines may be monoamines or polyamines. Useful amines include those amines disclosed in U.S. Pat. No. 4,234,435 at Col. 21, line 4 to Col. 27, line 50, these passages being incorporated herein by reference.

The monoamines generally contain a hydrocarbyl group which contains from 1 to about 30 carbon atoms, or from 1 to about 12, or from 1 to about 6 carbon atoms. Examples of primary monoamines useful in the present invention include methylamine, ethylamine, propylamine, butylamine, cyclopentylamine, cyclohexylamine, octylamine, dodecylamine, allylamine, cocoamine, stearyl-amine, and laurylamine. Examples of secondary monoamines include dimethylamine, diethylamine, dipropylamine, dibutylamine, dicyclopentylamine, dicyclohexylamine, methylbutylamine, ethylhexylamine, etc.

In one embodiment, the amine is a fatty ($C_{8-30}$) amine which include n-octylamine, n-decylamine, n-dodecylamine, n-tetradecylamine, n-hexadecyl-amine, n-octadecylamine, oleyamine, etc. Also useful fatty amines include commercially available fatty amines such as "Armeen" amines (products available from Akzo Chemicals, Chicago, Ill.), such as Armeen C, Armeen O, Armeen OL, Armeen T, Armeen HT, Armeen S and Armeen SD, wherein the letter designation relates to the fatty group, such as coco, oleyl, tallow, or stearyl groups.

Other useful amines include primary ether amines, such as those represented by the formula, $R"(OR')_xNH_2$, wherein R' is a divalent alkylene group having about 2 to about 6 carbon atoms; x is a number from one to about 150, or from about one to about five, or one; and R" is a hydrocarbyl group of about 5 to about 150 carbon atoms. An example of an ether amine is available under the name SURFAM® amines produced and marketed by Mars Chemical Company, Atlanta, Ga. Preferred etheramines are exemplified by those identified as SURFAM P14B (decyloxypropylamine), SURFAM P16A (linear $C_{16}$), SURFAM P17B (tridecyloxypropylamine). The carbon chain lengths (i.e., $C_{14}$, etc.) of the SURFAMS described above and used hereinafter are approximate and include the oxygen ether linkage.

In one embodiment, the amine is a tertiary-aliphatic primary amine. Generally, the aliphatic group, preferably an alkyl group, contains from about 4 to about 30, or from about 6 to about 24, or from about 8 to about 22 carbon atoms. Usually the tertiary alkyl primary amines are monoamines represented by the formula $R_5$—$C(R_6)_2$—$NH_2$, wherein $R_5$ is a hydrocarbyl group containing from one to about 27 carbon atoms and $R_6$ is a hydrocarbyl group containing from 1 to about 12 carbon atoms. Such amines are illustrated by tert-butylamine, tert-hexylamine, 1-methyl-1-amino-cyclohexane, tert-octylamine, tert-decylamine, tert-dodecylamine, tert-tetradecylamine, tert-hexadecylamine, tert-octadecylamine, tert-tetracosanylamine, and tert-octacosanylamine.

Mixtures of tertiary aliphatic amines may also be used in preparing the dithiocarbamic acid or salt. Illustrative of amine mixtures of this type are "Primene 81R" which is a mixture of $C_{11}$–$C_{14}$ tertiary alkyl primary amines and "Primene JMT" which is a similar mixture of $C_{18}$–$C_{22}$ tertiary alkyl primary amines (both are available from Rohm and Haas Company). The tertiary aliphatic primary amines and methods for their preparation are known to those of ordinary skill in the art. The tertiary aliphatic primary amine useful for the purposes of this invention and methods for their preparation are described in U.S. Pat. No. 2,945,749, which is hereby incorporated by reference for its teaching in this regard.

In one embodiment, the amine is a fatty ($C_{8-30}$) amine which include n-octylamine, n-decylamine, n-dodecylamine, n-tetradecylamine, n-hexadecyl-amine, n-octadecylamine, oleyamine, etc. Also useful fatty amines include commercially available fatty amines such as "Armeen" amines (products available from Akzo Chemicals, Chicago, Ill.), such Armeen C, Armeen O, Armeen OL, Armeen T, Armeen HT, Armeen S and Armeen SD, wherein the letter designation relates to the fatty group, such as coco, oleyl, tallow, or stearyl groups.

Other useful amines include primary ether amines, such as those represented by the formula, $R"(OR')_xNH_2$, wherein R' is a divalent alkylene group having about 2 to about 6 carbon atoms; x is a number from one to about 150, or from about one to about five, or one; and R" is a hydrocarbyl group of about 5 to about 150 carbon atoms. An example of an ether amine is available under the name SURFAM® amines produced and marketed by Mars Chemical Company, Atlanta, Ga. Preferred etheramines are exemplified by those identified as SURFAM P14B (decyloxypropylamine), SURFAM P16A (linear $C_{16}$), SURFAM P17B (tridecyloxypropylamine). The carbon chain lengths (i.e., $C_{14}$, etc.) of the SURFAMS described above and used hereinafter are approximate and include the oxygen ether linkage.

In one embodiment, the amine is a tertiary-aliphatic primary amine. Generally, the aliphatic group, preferably an alkyl group, contains from about 4 to about 30, or from about 6 to about 24, or from about 8 to about 22 carbon atoms. Usually the tertiary alkyl primary amines are monoamines represented by the formula $R_5$—$C(R_6)_2$—$NH_2$, wherein $R_5$ is a hydrocarbyl group containing from one to about 27 carbon atoms and $R_6$ is a hydrocarbyl group containing from 1 to about 12 carbon atoms. Such amines are illustrated by tert-butylamine, tert-hexylamine, 1-methyl-1-amino-cyclohexane, tert-octylamine, tert-decylamine, tert-dodecylamine, tert-tetradecylamine, tert-hexadecylamine, tert-octadecylamine, tert-tetracosanylamine, and tert-octacosanylamine.

Mixtures of tertiary aliphatic amines may also be used in preparing the dithiocarbamic acid or salt. Illustrative of amine mixtures of this type are "Primene 81R" which is a mixture of $C_{11}$–$C_{14}$ tertiary alkyl primary amines and "Primene JMT" which is a similar mixture of $C_{18}$–$C_{22}$ tertiary alkyl primary amines (both are available from Rohm and Haas Company). The tertiary aliphatic primary amines and methods for their preparation are known to those of ordinary skill in the art. The tertiary aliphatic primary amine useful for the purposes of this invention and methods for their preparation are described in U.S. Pat. No. 2,945,749, which is hereby incorporated by reference for its teaching in this regard.

In another embodiment, the amine is a secondary amine. Specific of secondary amines include dimethylamine, diethylamine, dipropylamine, dibutylamine, diamylamine, dihexylamine, diheptylamine, methylethylamine, ethylbutylamine, ethylamylamine and the like. In one embodiment, the secondary amine may be a cyclic amine, such as piperidine, piperazine, morpholine, etc.

In one embodiment, the amine may be a hydroxyamine. Typically, the hydroxyamines are primary, secondary or tertiary alkanol amines or mixtures thereof. Such amines can be represented by the formulae: $H_2N$—$R'$—$OH$, $HR'_1$—$N$—$R'$—$OH$, and $(R'_1)_2$—$N$—$R'$—$OH$, wherein each $R'_1$ is independently a hydrocarbyl group of one to about eight carbon atoms or hydroxyhydrocarbyl group having from two to about eight carbon atoms, preferably from one to about four, and $R'$ is a divalent hydrocarbyl group of about two to about 18 carbon atoms, preferably two to about four. The group —$R'$—$OH$ in such formulae represents the hydroxyhydrocarbyl group. $R'$ can be an acyclic, alicyclic or aromatic group. Typically, $R'$ is an acyclic straight or branched alkylene group such as an ethylene, 1,2-propylene, 1,2-butylene, 1,2-octadecylene, etc. group. Where two $R'$, groups are present in the same molecule they can be joined by a direct carbon-to-carbon bond or through a heteroatom (e.g., oxygen, nitrogen or sulfur) to form a 5-, 6-, 7- or 8-membered ring structure. Examples of such heterocyclic amines include N-(hydroxyl lower alkyl)-morpholines, -thiomorpholines, -piperidines, -oxazolidines, -thiazolidines and the like. Typically, however, each $R'_1$ is independently a methyl, ethyl, propyl, butyl, pentyl or hexyl group. Examples of these alkanolamines include mono-, di-, and triethanolamine, diethylethanolamine, ethylethanolamine, butyldiethanolamine, etc.

The hydroxyamines can also be an ether N-(hydroxyhydrocarbyl)amine. These are hydroxypoly (hydrocarbyloxy) analogs of the above-described hydroxy amines (these analogs also include hydroxyl-substituted oxyalkylene analogs). Such N-(hydroxyhydrocarbyl) amines can be conveniently prepared by reaction of epoxides with aforedescribed amines and can be represented by the formulae: $H_2N$—$(R'O)_X$—$H$, $HR'_1$—$N$—$(R'O)_X$—$H$, and $(R'_1)_2$—$N$—$(R'O)_X$—$H$, wherein x is a number from about 2 to about 15 and $R_1$ and $R'$ are as described above. $R'_1$ may also be a hydroxypoly(hydrocarbyloxy) group.

In another embodiment, the amine is a hydroxyhydrocarbyl amine which contains at least one NH group. Useful hydroxyhydrocarbyl amine may be represented by the formula

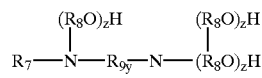

wherein $R_7$ is a hydrocarbyl group generally containing from about 6 to about 30 carbon atoms; $R_8$ is an alkylene group having from about two to about twelve carbon atoms, preferably an ethylene or propylene group; $R_9$ is an alkylene group containing up to about 5 carbon atoms; y is zero or one; and each z is independently a number from zero to about 10, with the proviso that at least one z is zero.

Useful hydroxyhydrocarbyl amines where y in the above formula is zero include 2-hydroxyethylhexylamine; 2-hydroxyethyloctylamine; 2-hydroxyethylpentadecylamine; 2-hydroxyethyloleylamine; 2-hydroxyethylsoyamine; bis(2-hydroxyethyl)hexylamine; bis(2-hydroxyethyl)oleylamine; and mixtures thereof. Also included are the comparable members wherein in the above formula at least one z is at least 2, as for example, 2-hydroxyethoxyethyl, hexylamine.

In one embodiment, the amine may be a hydroxyhydrocarbyl amine, where referring to the above formula, y equals zero. These hydroxyhydrocarbyl amines are available from the Akzo Chemical Division of Akzona, Inc., Chicago, Ill., under the general trade designations "Ethomeen" and "Propomeen". Specific examples of such products include: Ethomeen C/15 which is an ethylene oxide condensate of a coconut fatty acid containing about 5 moles of ethylene oxide; Ethomeen C/20 and C/25 which are ethylene oxide condensation products from coconut fatty acid containing about 10 and 15 moles of ethylene oxide, respectively; Ethomeen O/12 which is an ethylene oxide condensation product of oleyl amine containing about 2 moles of ethylene oxide per mole of amine; Ethomeen S/15 and S/20 which are ethylene oxide condensation products with stearyl amine containing about 5 and 10 moles of ethylene oxide per mole of amine, respectively; Ethomeen T/12, T/15 and T/25 which are ethylene oxide condensation products of tallow amine containing about 2, 5 and 15 moles of ethylene oxide per mole of amine, respectively; and Propomeen O/12 which is the condensation product of one mole of oleyl amine with 2 moles propylene oxide.

In one embodiment, the amine is a polyamine. The polyamines include alkoxylated diamines, fatty polyamine diamines, alkylenepolyamines, hydroxy containing polyamines, condensed polyamines arylpolyamines, and heterocyclic polyamines. Commercially available examples of alkoxylated diamines include those amines where y in the above formula is one. Examples of these amines include Ethoduomeen T/13 and T/20 which are ethylene oxide condensation products of N-tallowtrimethylenediamine containing 3 and 10 moles of ethylene oxide per mole of diamine, respectively.

In another embodiment, the polyamine is a fatty diamine. The fatty diamines include mono- or dialkyl, symmetrical or asymmetrical ethylene diamines, propane diamines (1,2, or 1,3), and polyamine analogs of the above. Suitable commercial fatty polyamines are Duomeen C (N-coco-1,3-diaminopropane), Duomeen S (N-soya-1,3-diaminopropane), Duomeen T (N-tallow-1,3-diaminopropane), and Duomeen O (N-oleyl-1,3-diaminopropane). "Duomeens" are commercially available from Armak Chemical Co., Chicago, Ill.

Alkylene polyamines are represented by the formula $HR_{10}N$-$(Alkylene$-$N)_n$—$(R_{10})_2$, wherein n has an average value from 1 to about 10, or from about 2 to about 7, or from about 2 to about 5, and the "Alkylene" group has from 1 to about 10 carbon atoms, or from about 2 to about 6, or from about 2 to about 4. In one embodiment, each $R_{10}$ is independently hydrogen; or an aliphatic or hydroxy-substituted aliphatic group of up to about 30 carbon atoms In another embodiment, $R_{10}$ is defined the same as $R'_1$ above.

Such alkylenepolyamines include methylenepolyamines, ethylenepolyamines, butylenepolyamines, propylenepolyamines, pentylenepolyamines, etc. The higher homologs and related heterocyclic amines such as piperazines and N-amino alkyl-substituted piperazines are also included. Specific examples of such polyamines are ethylenediamine, triethylenetetramine, tris-(2-aminoethyl) amine, propylenediamine, trimethylenediamine, tripropylenetetramine, tetraethylenepentamine, hexaethyleneheptamine, pentaethylenehexamine, etc.

Higher homologs obtained by condensing two or more of the above-noted alkyleneamines are similarly useful as are mixtures of two or more of the aforedescribed polyamines.

In one embodiment the polyamine is an ethylenepolyamine. Such polyamines are described in detail under the heading Ethylene Amines in Kirk Othmer's "Encyclopedia of Chemical Technology", 2d Edition, Vol. 7, pages 22–37, Interscience Publishers, New York (1965). Ethylenepolyamines are often a complex mixture of polyalkylenepolyamines including cyclic condensation products.

Other useful types of polyamine mixtures are those resulting from stripping of the above-described polyamine mixtures to leave, as residue, what is often termed "polyamine bottoms". In general, alkylenepolyamine bottoms can be characterized as having less than 2%, usually less than 1% (by weight) material boiling below about 200° C. A typical sample of such ethylene polyamine bottoms obtained from the Dow Chemical Company of Freeport, Tex. designated "E-100" has a specific gravity at 15.6° C. of 1.0168, a percent nitrogen by weight of 33.15 and a viscosity at 40° C. of 121 centistokes. Gas chromatography analysis of such a sample contains about 0.93% "Light Ends" (most probably DETA), 0.72% TETA, 21.74% tetraethylenepentaamine and 76.61% pentaethylenehexamine and higher (by weight). These alkylenepolyamine bottoms include cyclic condensation products such as piperazine and higher analogs of diethylenetriamine, triethylenetetramine and the like.

These alkylenepolyamine bottoms can be reacted solely with the acylating agent or they can be used with other amines, polyamines, or mixtures thereof.

Another useful polyamine is the product of a condensation reaction between at least one hydroxy compound with at least one polyamine reactant containing at least one primary or secondary amino group. The hydroxy compounds are preferably polyhydric alcohols and amines. The polyhydric alcohols are described below. (See carboxylic ester dispersants.) In one embodiment, the hydroxy compounds are polyhydric amines. Polyhydric amines include any of the above-described monoamines reacted with an alkylene oxide (e.g., ethylene oxide, propylene oxide, butylene oxide, etc.) having from two to about 20 carbon atoms, or from two to about four. Examples of polyhydric amines include tri-(hydroxypropyl)amine, tris-(hydroxymethyl) amino methane, 2-amino-2-methyl-1,3-propanediol, N,N, N',N'-tetrakis(2-hydroxyethyl)ethylenediamine, and N,N,N', N'-tetrakis(2-hydroxyethyl)ethylenediamine, preferably tris (hydroxymethyl)aminomethane (THAM). The condensation reaction of the polyamine reactant with the hydroxy compound is conducted at an elevated temperature, usually from about 60° C. to about 265° C., or from about 220° C. to about 250° C. in the presence of an acid catalyst.

Polyamines which react with the polyhydric alcohol or amine to form the condensation products or condensed amines, are described above. Preferred polyamines include triethylenetetramine (TETA), tetraethylenepentamine (TEPA), pentaethylenehexamine (PEHA), and mixtures of polyamines such as the above-described "amine bottoms".

In one embodiment, the polyamines are polyoxyalkylene polyamines, e.g., polyoxyalkylene diamines and polyoxyalkylene triamines, having average molecular weights ranging from about 200 to about 4000 or from about 400 to about 2000. The preferred polyoxyalkylene polyamines include the polyoxyethylene and polyoxypropylene diamines and the polyoxypropylene triamines. The polyoxyalkylene polyamines are commercially available and may be obtained, for example, from the Jefferson Chemical Company, Inc. under the trade name "Jeffamines D-230, D-400, D-1000, D-2000, T-403, etc.". U.S. Pat. Nos. 3,804, 763 and 3,948,800 are expressly incorporated herein by reference for their disclosure of such polyoxyalkylene polyamines and acylated products made therefrom.

In another embodiment, the polyamines are hydroxy-containing polyamines. Hydroxy-containing polyamine analogs of hydroxy monoamines, particularly alkoxylated alkylenepolyamines, e.g., N,N(diethanol)ethylene diamines can also be used. Such polyamines can be made by reacting the above-described alkylene amines with one or more of the above-described alkylene oxides. Similar alkylene oxide-alkanol amine reaction products may also be used such as the products made by reacting the above described primary, secondary or tertiary alkanol amines with ethylene, propylene or higher epoxides in a 1.1 to 1.2 molar ratio. Reactant ratios and temperatures for carrying out such reactions are known to those skilled in the art.

Specific examples of alkoxylated alkylenepolyamines include N-(2-hydroxyethyl) ethylenediamine, N,N'-bis(2-hydroxyethyl)-ethylene-diamine, 1-(2-hydroxyethyl) piperazine, mono(hydroxypropyl)-substituted tetraethylenepentamine, N-(3-hydroxybutyl)-tetramethylene diamine, etc. Higher homologs obtained by condensation of the above illustrated hydroxy-containing polyamines through amino groups or through hydroxy groups are likewise useful. Condensation through amino groups results in a higher amine accompanied by removal of ammonia while condensation through the hydroxy groups results in products containing ether linkages accompanied by removal of water. Mixtures of two or more of any of the above described polyamines are also useful.

In another embodiment, the amine is a heterocyclic polyamine. The heterocyclic polyamines include aziridines, azetidines, azolidines, tetra- and dihydropyridines, pyrroles, indoles, piperidines, imidazoles, di- and tetrahydroimidazoles, piperazines, isoindoles, purines, morpholines, thiomorpholines, N-aminoalkylmorpholines, N-aminoalkylthiomorpholines, N-aminoalkyl-piperazines, N,N'-diaminoalkylpiperazines, azepines, azocines, azonines, azecines and tetra-, di- and perhydro derivatives of each of the above and mixtures of two or more of these heterocyclic amines. Preferred heterocyclic amines are the saturated 5- and 6-membered heterocyclic amines containing only nitrogen, oxygen and/or sulfur in the hetero ring, especially the piperidines, piperazines, thiomorpholines, morpholines, pyrrolidines, and the like. Piperidine, aminoalkyl substituted piperidines, piperazine, aminoalkyl substituted piperazines, morpholine, aminoalkyl substituted morpholines, pyrrolidine, and aminoalkyl-substituted pyrrolidines, are especially preferred. Usually the aminoalkyl substituents are substituted on a nitrogen atom forming part of the hetero ring. Specific examples of such heterocyclic amines include N-aminopropylmorpholine, N-aminoethylpiperazine, and N,N'-diaminoethylpiperazine. Hydroxy heterocyclic polyamines are also useful. Examples include N-(2-hydroxyethyl)cyclohexylamine, 3-hydroxycyclopentylamine, parahydroxyaniline, N-hydroxyethylpiperazine, and the like.

Hydrazine and hydrocarbyl substituted-hydrazine can also be used to form the acylated nitrogen dispersants. At least one of the nitrogen atoms in the hydrazine must contain a hydrogen directly bonded thereto. Preferably there are at least two hydrogens bonded directly to hydrazine nitrogen and, more preferably, both hydrogens are on the same nitrogen. Specific examples of substituted hydrazines are methylhydrazine, N,N-dimethyl-hydrazine, N,N'-dimethylhydrazine, phenylhydrazine, N-phenyl-N'-ethylhydrazine, N-(para-tolyl)-N'-(n-butyl)-hydrazine, N-(para-nitrophenyl)-hydrazine, N-(para-nitrophenyl)-N-methyl-hydrazine, N,N'-di(para-chlorophenol)-hydrazine, N-phenyl-N'-cyclohexylhydrazine, and the like.

In another embodiment, the amines may be polyamidoamines, cycloaliphatic amines, aromatic amines, ketimines, etc. The use of aromatic amines such as MPDA or MDA provide for longer polymerization times which permit baking on media for specific applications. Ketimines (amines reacted with ketones) may be used to add unreacted sols of amine and ketone to a polymerization (media formation) which can be removed after cure by water or moisture in order to facilitate desired media properties. The ketimines provide a mechanism to effect porosity or water permeability as components of the whole biodegradation process desired in a stenoprophiluric media.

In one embodiment, the cross-linking agent may be a polyhydroxy compound. The polyhydroxy compound includes compounds of the general formula $R''(OH)_m$ wherein R" is a monovalent or polyvalent organic group joined to the —OH groups through a carbon bond, and m is an integer of from 1 to about 10 wherein the hydrocarbyl group contains at least about 8 aliphatic carbon atoms. The hydroxy compounds may be aliphatic compounds, such as polyhydric alcohols.

In one embodiment, the cross-linking agent is a polyhydric alcohol such as those described herein. In one embodiment, the polyhydric alcohols generally contain up to about 40 aliphatic carbon atoms, or from 2 to about 30, or from 2 to about 10. The polyhydric alcohols contain from 2 to about 40 carbon atoms, from 2 to about 20; and from 2 to about 10 hydroxyl groups, or from 2 to about 6. Polyhydric alcohols include ethylene glycols, including di-, tri- and tetraethylene glycols; propylene glycols, including di-, tri- and tetrapropylene glycols; glycerol; butanediol; hexanediol; sorbitol; arabitol; mannitol; sucrose; fructose; glucose; cyclohexanediol; erythritol; and pentaerythritols, including di- and tripentaerythritol; preferably, diethylene glycol, triethylene glycol, glycerol, sorbitol, pentaerythritol and dipentaerythritol.

The polyhydric alcohols may be esterified with monocarboxylic acids having from 2 to about 30 carbon atoms, or from about 8 to about 18, provided that at least one hydroxyl group remains unesterified. Examples of monocarboxylic acids include acetic, propionic, butyric and fatty carboxylic acids. The fatty monocarboxylic acids have from about 8 to about 30 carbon atoms and include octanoic, oleic, stearic, linoleic, dodecanoic and tall oil acids. Specific examples of these esterified polyhydric alcohols include sorbitol oleate, including mono- and dioleate, sorbitol stearate, including mono- and distearate, glycerol oleate, including glycerol mono-, di- and trioleate and erythritol octanoate.

Polymers

Some examples of polymers useful in preparing the stenoprophiluric media include phenyl resins, acrylic resins, nitrocellulose resins, alkyd resins, maleated resins, rubbers, including chlorinated rubbers, styrene or isoprenebutadiene rubbers, etc., melamine resins, styrenated, acrylated, maleated or cyclopentadiene reacted oils, silicone polymers, epoxy resins, polyester resins, polyurethane resins, polyvinyl chlorides, polytetrafluoroethylene, amino resins, and the like.

Some specific polymers include examples of useful stenoprophiluric polymers include one or more of phenol-formaldehyde resin, acrylic resins, rosin modified phenolics, phenolic resins, cellulose and nitrocellulose resins, alkyd resins, maleated rosins, varnishes, oil soluble phenolic resins, chlorinated rubbers, urea formaldehydes, vinyl chloride, oil based emulsions, polyvinyl butyrals, melamine formaldehyde, styrenated, acrylated and cyclopentadiene-reacted oils, silicone resins and polymers, styrene-butadiene polymers, polyvinyl acetate, epoxy resins, unsaturated polyester resins, epoxy/polyamide blends, thixotrophic alkyd resins, water soluble/dispersible thermosetting resins (alkyds, acrylics), urethane oils and alkyds, thermoplastic acrylics, thermosetting acrylics, silicone copolymers, powder coatings, fluidized bed powder coatings, Epoxy and acrylic electro-deposited, fluoropolymers, ultraviolet and electron beam curable polymers, non-aqueous dispersions, non-aqueous dispersion acrylics, epoxy and acrylic and other resins-cathodically electrodeposited, interpenetrating polymer networks, acrylic and polyester and urethane oligomers for high solids, group transfer polymerized, high solids resins, polymers with reactive diluents, waterborne resins, lacquers, including acrylic and halogenated lacquers, polyvinyl chloride, latexes, chlorinated ethylene-vinyl acetate copolymers, polytetrafluoroethylene, acrylic latexes, vinyl ester latexes, vinyl acetate, polyurethane dispersions, urethanes, urethane dispersions, hybrid urethane-acrylic dispersions, acrylic polyols, polyester polyols, amino resin cured polyols, isocyanate crosslinked aliphatic resins, benzoguanamine-formaldehyde, glycouril, isocyanates, oxirane epoxy, bisphenol-A, triphenylphosphine, bisphenol-F, novolacs, epichlohydrin, aromatic amines, m-phenylene diamine, waterborne epoxy-amine, mercaptan crosslinked epoxides, polysulfide resins, acid and anhydride crosslinked acrylic and polyester resins, epoxide homopolymers, resole phenolic resins, epoxy novolacs, cathodic electrodeposited resins, natural oils, 18 carbon, oleic and linoleic and linolenic fatty acids, modified oils; heat bodied, blown, dehydrated, maleated, and varnishes, linseed alkyds, monoglyceride processed, styrenated and vinyl modified alkyds, epoxy esters, unsaturated polyesters, insoluble crystalline wax formulated, oxygen scavengered polymers, radiation cured, silicone modified alkyds, silicone resins, silanol group, inorganic zinc rich or zinc silicates, acetoacetate, aldehydes, formaldehyde, Michael acceptor and reactor, aziridines, polycarbodiimides, analogs, precursors, intermediates, blends, mixes, combinations, adducts, reactants, and phases of the above.

Suitable examples of thermoplastic resins for the media of the present invention include acrylics, vinyls, high styrene resins, chlorinated rubber, cellulosic esters, and cellulosic ethers. Specific examples include polyethylene, polypropylene, polytetra-fluoroethylene, polyvinyl chloride, polyvinyl chloride/polyvinyl acetate, polystyrene, polyacrylates and polymethacrylates, nitrocellulose, polyvinyl butyral, polyvinylidene chloride and styrene butadiene. Suitable examples of thermoplastic resins include polyolefins, including low density polyethylene (LDPE) and polypropylene, polyvinylchloride (PVC), polyamides, polyesters, chlorinated polyethers, and cellulose-acetobutyrate. What follows is a brief description of some of the film forming resins which may be used in accordance with this invention. A brief description of the curatives and/or curing reactions is also included when the resin is also used as a thermosetting resin.

In one embodiment, the stenoprophiluric media contains a thermosetting resin. Thermosetting resins include urethanes, amino resins, acrylic resins, alkyd resins, epoxy resins, phenolic resins, cyclized olefin rubbers, halogenated polyolefins, halo-sulfonated polyolefins, polybutadiene rubbers, natural resins, and mixtures thereof.

Epoxy

In one embodiment, the stenoprophiluric media comprises at least one epoxy resin. A wide variety of epoxy resins may be used in the present invention. Generally, the epoxy resins will have a molecular weight from about 300 to about 100,000. More generally, the epoxy resins will have an epoxide equivalent weight from about 150 to about 10,000, or an epoxide equivalent weight from about 1000 to about 3000, or from about 1550–2500. Here and elsewhere in the specification and claims the range and ratio limits may be combined. The epoxy resins used in this invention may be any one of a number of well known epoxy resins which are characterized by the presence therein of at least one epoxide group. As used in the specification and in the appended claims, the term "epoxy resin" is intended to describe the reaction products of the condensation reaction of an epihalohydrin and a hydroxy-containing compound or carboxylic acid.

Thermosetting epoxy resins include any of a number of well-known organic resins which are characterized by the presence therein of the epoxide or oxirane group a wide variety of such resins are available commercially. Examples of epoxy resins based on the epoxide group; diglycidyl ether of bisphenol-A, novolacs, resole resins, waterborne epoxy amines, phenolic resins-cationic. Such resins have either a mixed aliphatic-aromatic or an exclusively non-benzeneoid (i.e., aliphatic or cycloaliphatic) molecular structure.

The epoxy resins may be of the ether or ester types. Examples of ester-type epoxy resins include polyglycidyl esters obtainable by reaction of a compound containing two or more carboxylic acid groups per molecule with epichlorohydrin or glycerol dichlorohydrin in the presence of an alkali. Such polyglycidyl esters may be derived from aliphatic polycarboxylic acids, e.g., succinic acid, glutaric acid, adipic acid, pimelic acid, suberic acid, azelaic acid, sebacic acid, or dimerised or trimerised linoleic acid; from cycloaliphatic polycarboxylic acids such as tetrahydrophthalic acid, 4-methyltetrahydrophthalic acid, hexahydrophthalic acid, and 4-methylhexahydrophthalic acid; and from aromatic polycarboxylic acids such as phthalic acid, isophthalic acid, and terephthalic acid.

Ether-type epoxy resins are obtained by reaction of a compound containing at least two free alcoholic hydroxyl and/or phenolic hydroxyl groups per molecule with an epihalohydrin under alkaline conditions, or in the alternative, in the presence of an acidic catalyst with subsequent treatment with an alkali. The products of such reactions instead of being single simple compounds are generally complex mixtures of glycidyl polyethers. These ethers may be made from acyclic alcohols, such as ethylene glycol, diethylene glycol, and higher poly(oxyethylene) glycols, propane-1,2-diol and poly(oxypropylene) glycols, propane-1,3-diol, poly(oxytetramethylene) glycols, pentane-1,5-diol, hexane-2,4,6-triol, glycerol, 1,1,1-trimethylolpropane, pentaerythritol, sorbitol, and polyepichlorohydrins; from cycloaliphatic alcohols such as resorcitol, quinitol, bis(4-hydroxycyclohexyl)methane, and 2,2-bis(4-hydroxycyclohexyl) propane, and from alcohols having aromatic nuclei, such as N,N-bis(2-hydroxyethyl) aniline and p,p'bis(2-hydroxyethylamino) diphenylmethane. Or they may be made from mononuclear phenols, such as resorcinol and hydroquinone, and from polynuclear phenols, such as bis(4-hydroxyphenyl) methane (otherwise known as bisphenol F), 4,4'-dihydroxydiphenyl, bis(4-hydroxyphenyl) sulphone, 1,1,2,2-tetrakis(4-hydroxyphenyl) ethane, 2,2-bis(4-hydroxyphenyl)propane, (otherwise known as bisphenol A), 2,2-bis(3,5-dibromo-4-hydroxyphenyl)propane, and novolacs formed from aldehydes such as formaldehyde, acetaldehyde, chloral, and furfuraldehyde, with phenol itself, and phenol substituted in the ring by chlorine atoms or by alkyl groups each containing up to 9 carbon atoms, such as 4-chlorophenol, 2-methylphenol, and 4-tert-butylphenol.

In one embodiment, the epoxy resins have either a mixed aliphatic aromatic or an exclusively non-benzenoid (i.e., aliphatic or cycloaliphatic) molecular structure. The mixed aliphatic-aromatic epoxy resins generally are prepared by the well-known reaction of a bis-(hydroxy-aromatic) alkane or a tetrakis-(hydroxy-aromatic) alkane with a halogen-substituted aliphatic epoxide in the presence of a base such as, for example, sodium hydroxide or potassium hydroxide. In one preferred embodiment, the epoxy resins are diglycidyl ethers of bisphenols, especially bisphenol A. These are made by reacting epichlorohydrin with bisphenol A in the presence of an alkaline catalyst. By controlling the operating conditions and varying the ratio of epichlorohydrin to bisphenol A, products of different molecular weight can be made.

The mixed aliphatic-aromatic epoxy resins are prepared by the well-known reaction of a bis(hydroxy-aromatic) alkane or a tetrakis-(hydroxyaromatic)-alkane with a halogen-substituted aliphatic epoxide in the presence of a base such as, e.g., sodium hydroxide or potassium hydroxide. Under these conditions, hydrogen halide is first eliminated and the aliphatic epoxide group is coupled to the aromatic nucleus via an ether linkage. Then the epoxide groups condense with the hydroxyl groups to form polymeric molecules which vary in size according to the relative proportions of reactants and the reaction time.

In lieu of the epichlorohydrin, one can use halogen-substituted aliphatic epoxides containing 2 or more carbon atoms, generally 2 to about 20, or from 3 to about 12 carbon atoms. In general, a chlorine-substituted terminal alkylene oxide (terminal denoting that the epoxide group is on the end of the alkyl chain), such as epichlorohydrin are useful by reason of its commercial availability and excellence in forming epoxy resins useful for the purpose of this invention.

If desired, the halogen-substituted aliphatic epoxide may also contain substituents such as, e.g., hydroxy, keto, nitro, nitroso, ether, sulfide, carboalkoxy, etc.

Similarly, in lieu of the 2,2-bis-(p-hydroxyphenyl)-propane, bis-(hydroxyaromatic) alkanes containing about 16 or more carbon atoms, generally about 16 to about 30 carbon atoms can be used. Examples of these materials include 2,2-bis-(1-hydroxy-4-naphthyl)-propane; 2,2-bis(o-hydroxyphenyl)propane; 2,2-bis-(p-hydroxyphenyl) butane, 3,3-bis-(p-hydroxyphenyl)hexane; 2-(p-hydroxyphenyl)-4-(1-hydroxy-4-naphthyl)octane, 5-5-bis-(p-hydroxy-o-methylphenyl)-decane, bis-(p-hydroxyphenyl) methane, 2,2-bis-(p-hydroxy-o-isopropylphenyl)propane, 2,2-b is-(o, p-dihydroxyphenyl)propane, 2-(p-hydroxyphenyl)-5-(o-hydroxyphenyl)hexadecane, and the like. If desired, the bis-(hydroxyaromatic)alkane may contain substituents such as, e.g., halogen, nitro, nitroso, ether, sulfide, carboalkoxy, etc.

Other usable epoxy resins include the diglycidyl ethers of other bisphenol compounds such as bisphenol B, F, G and H. Epoxy resins of the type described above based on various bisphenols are available from a wide variety of commercial sources. One group is known by the general trade designation "Epon" resins and are available from Shell Chemical Company. For example, "Epon 820" is an epoxy resin having an average molecular weight of about 380 and is prepared from 2,2-bis-(p-hydroxyphenyl) propane and epichlorohydrin. Similarly, "Epon 1031" is an epoxy resin having an average molecular weight of about 616 and is prepared from epichlorohydrin and symmetrical tetrakis-(p-hydroxyphenol) ethane. "Epon 828" has a molecular weight of 350–400 and an epoxide equivalent of about 175–210. "Epon 1001" is an epoxy resin having an average molecular weight of about 1000 and an epoxide equivalent weight of 500. "Epon 1007" has an average molecular weight of about 4500 and an epoxy equivalency of about 1850 to about 2300. "Epon 1009" has an epoxide equivalent of about 2400–4000. One group is known by the general trade designation "Epon" resins and are available from Shell Chemical Co.

Another group of commercially available epoxy resins is identified under the general trade designation EPI-REZ (Celanese Resins, a division of Celanese Coatings Company). For example, EPI-REZ 510 and EPI-REZ 509 are commercial grades of the diglycidyl ether or bisphenol A differing slightly in viscosity and epoxide equivalent. EPI-REZ 522F is a bisphenol A-epichlorohydrin resin with an epoxy equivalency of about 600.

Another group of epoxy resins are available from Furane Plastics Inc., Los Angeles, Calif. under the general trade designations EPIBOND and EPOCAST. For example, EPI-BOND 100A is a one component epoxy resin powder available from Furane which is curable to a hard resin in the absence of any hardener.

Liquid forms of epoxy resin are also useful. These liquid forms normally comprise very viscous liquids requiring some degree of heating to permit withdrawal from storage containers. Certain "D.E.R." resins obtainable from Dow Chemical Company and "EPOTUF" liquid epoxy resins obtainable from Reichhold Chemicals Inc. are examples of such resins preferred for employment in accordance with the invention. An example of an "Epotuf" liquid epoxy resin in the undiluted medium high viscosity #37–140 having an epoxide equivalent weight of 180–195, a viscosity (ASTM D445) of 11,000–14,000 cps at 25.degree. C., and a Gardner Color Maximum of 3. This is a standard general purpose epoxy resin.

Another class of epoxy resins useful in the present invention is the epoxidized novolacs, particularly the epoxy cresol and epoxy phenol novolacs.

These are produced by reacting a novolac resin, usually formed by the reaction of orthocresol or phenol and formaldehyde with epichlorohydrin. Epoxy resins derived from non-benzenoid materials, such as aliphatic or cycloaliphatic hydroxy-containing compounds, also can be utilized in the present invention. Epoxy resins having non-benzenoid molecular structures generally are referred to in the art as being aliphatic epoxy resins or cycloaliphatic epoxy resins. Cycloaliphatics can be produced by the peracetic epoxidation of cyclic olefins and by the condensation of an acid such as tetrahydrophthalic with epichlorohydrin, followed by dehydrohalogenation. The aliphatic epoxy resins can be prepared by reacting hydroxy-containing aliphatic and cycloaliphatic compounds such as aliphatic diols and triols.

For example, ethylene glycol or glycerol can be reacted with a halogen-substituted aliphatic epoxide such as epichlorohydrin (and others mentioned above) to form liquid epoxy resins characterized by viscosities which are lower than epoxy resins derived from aromatic hydroxy compounds. When cured, such aliphatic epoxy resins are not as brittle as the aromatic epoxy resins, and in many instances, exhibit elastomeric properties. Aliphatic epoxy resins are available commercially from a variety of sources including, for example, Shell Chemical Company and Reichhold Chemicals, Inc. Specific examples include Epon 562 from Shell Chemical Company having a viscosity of 90–150 centipoises at about 23° C., an epoxide equivalent of 140–165, and a hydroxyl equivalent weight of about 65. The epoxy resins will have an epoxy equivalency greater than 1.0. By epoxy equivalence, reference is made to the average number of 1,2-epoxide groups contained in the average molecule of the glycidyl ether or ester. As a result of the method of preparing the glycidyl polyethers and polyesters, and since they are ordinarily mixtures of chemical compounds having somewhat different molecular weights, the epoxy equivalency of the products is not necessarily the integer 2.0. However, the equivalency is generally a value between 1.0 and 2.0. Epoxidized novolac resins generally are prepared by the reaction of epichlorohydrin with phenol formaldehyde condensates. The epoxidized novolacs may contain more than two epoxy groups per molecule, and epoxidized novolacs having up to 7 to more epoxy groups are available commercially. The use of epoxidized novolacs containing more than two epoxy groups per molecule results in products containing a highly cross-linked structure. Ultra-high molecular weight epoxy resins also may be used in the invention. A group of such resins is available from the Shell Chemical Company under the general trade designation "Eponol". The ultra-high molecular weight resins are derived from bisphenol-A and epichlorohydrin and are available commercially as Eponol Resin 53-BH-35 and Eponol Resin 55-BH-30, In one embodiment, the media comprises an epoxy resin and at least one halogen-containing thermoplastic polymer. Halogen-containing vinyl polymers and copolymers, including vinylidene chloride homopolymers and copolymers are useful in combination with the epoxy resins. Vinylidene chloride copolymers include copolymers of vinylidene chloride with vinyl chloride, acrylates or nitrites, the choice of comonomers being dependent upon the properties desired. Polyvinylidene fluoride resins useful in combination with the epoxy resins of the present invention are available commercially from a variety of sources including Pennwalt Corporation. One specific example of a polyvinylidene fluoride available from Pennwalt is Kynar 500 resin.

The resin component of the aqueous compositions of the present invention also may comprise mixtures of epoxy resins with other resins capable of modifying the properties of the epoxy resin such as amine-formaldehyde resins, phenol-formaldehyde resins, polyamide resins, urea resins, polyolefins, polyesters, etc.

In another embodiment, the epoxy resins may be "solubilized" by neutralization with a basic compound such as an organic amine. Examples of amines include amines and hydroxyamines, including polyamines and hydroxy polyamines described below. Examples of amines include diethylamine, triethylamine, triethanolamine, dimethylethanolamine, etc. The epoxy resins may also be "solubilized" by neutralization with an acid. An example of a commercially available useful acid neutralized water reducible epoxy resin is resin K-5276 available from The Glidden Company.

Epoxy esters may be prepared by forcing a high temperature reaction with a stoichiometry of two fatty acids to one epoxide group and one with each OH group present in the epoxy resin produces a greater than 90% reaction success. These materials (epoxy esters) have excellent adhesion to metal properties and can be processed with appropriate agents to fit a 1.5 to 2.5 mil/year degradation rate. The epoxy ester contains no hydrolyzable group.

Epoxy or phenolic resins may be prepared using polyamides and a clay catalyst to prevent separation in stored intermediates and/or support the formation of a desired media.

Imidazolines may be used in an epoxy resin to provide greater compatibility of media or polymer formation with such materials as coal tar resins and other naturally occurring substances such as cellulose, and nitrocellulose. These materials may be additives, and/or nutrients.

In one embodiment, epoxy resins are blended with acrylic copolymers containing glycidal methacrylate to reduce susceptibility of the polymer to excess UV acceleration of the biodegradation rate. Alternatively cycloalipahtic epoxides may be used together with or in place of the glycidal methacrylate.

In one embodiment, epoxy resin polymer is used to prepare the media, wherein the N—H groups (amine hydrogen functionality) of the polymer is adjusted to modify the cure rate permitting preferred adducts and consequential cross-link structure. This cross-linking may occur when the inert additives of the media exceed 30% by weight.

Use may be made of a media formed from an epoxide which contains mercaptans, phenols or combinations of these as agents in the final polymer where the phenols and/or mercaptans are in stoichiometric excess for formation of media.

In one embodiment, the media is prepared using novolac resin and the media includes a natural oil, such as those described herein. Examples of useful oils include tung oil, linseed oil, and other natural substances.

An epoxy or phenolic resin where epichlorohydrin is used to decrease the ultimate cross-link density to reach a targeted biodegradation rate for a specific host habitat.

Use may be made of formation of a media with an isocyanate formulation where either tertiary amines, metal salts, and chelates, and organometallic compounds are used as combinations to provide a stenoprophiluric media, i.e., organotin. The level of tin under the principles of stenoprophiluricity will be at a concentration that does not toxify all organisms and maintains the goal of "no release" to the environment.

Aminoplast

In one embodiment, the stenoprophiluric media comprises an aminoplast resin. The amino resins (sometimes referred to as aminoplast resins or polyalkylene amides) are nitrogen-rich polymers containing nitrogen in the amino form, —NH$_2$. The starting amino-bearing material is usually reacted with an aldehyde (e.g., formaldehyde) to form a reactive monomer, which is then polymerized to a thermosetting resin. Examples of amino-bearing materials include urea, melamine, copolymers of both with formaldehyde, thiourea, aniline, dicyanodiamide, toluene sulfonamide, benzoguanamine, ethylene urea and acrylamide. Examples of useful amino resins include the melamine-formaldehyde and urea-formaldehyde resins.

Condensation products of other amines and amides can also be employed, for example, aldehyde condensates of triazines, diazines, triazoles, guanadines, guanamines and alkyl- and aryl-substituted derivatives of such compounds including alkyl- and aryl-substituted ureas and alkyl- and aryl-substituted melamines. Some examples of such compounds are N,N'-dimethylurea, benzourea, dicyandiamide, 2-chloro-4,6-diamino-1,3,5-triazine and 3,5-diaminotriazole. Other examples of melamine and urea-based cross-linking resins include alkylated melamine resins including methylated melamine-formaldehyde resins, such as hexamethoxymethyl melamine, alkoxymethyl melamines and ureas in which the alkoxy groups have 1–4 carbon atoms such as methoxy, ethoxy, propoxy, or butoxymethyl melamines and dialkoxymethyl ureas; alkylol melamines and ureas, such as hexamethylol melamine and dimethylol urea. The aminoplast cross-linking resins may be used in combination with another thermosetting resin such as an alkyd resin, a polyester resin, an epoxy resin or an acrylic resin.

Aminoplast resins are based on the addition products of aldehydes such as formaldehyde with an amino- or amido-group carrying substance. Condensation products obtained from the reactions of formaldehyde with melamine, urea or benzoguanamine are most common. These condensation products can be monomeric or polymeric.

Melamine-formaldehyde and urea-formaldehyde resins are useful in the stenprophiluric media. These resins are used primarily as cross-linkers for hydroxyl-bearing resins. Melamine-formaldehyde and urea-formaldehyde resins are the products of the reaction of formaldehyde with melamine or urea. Either melamine or urea resins (or mixtures thereof may be used as the cross-linking agents, although the melamines generally provide a greater degree of cross-linking. Useful melamine and urea resins are the alkoxy alkyl and the alkylol melamines and ureas. Specific examples include: alkoxymethyl melamines and ureas in which the alkoxy groups have 1–4 carbon atoms such as hexa-alkoxy (methoxy, ethoxy, propoxy, butoxy and mixed alkoxy) methyl melamines and dialkoxy methyl ureas; and the alkylol melamines and ureas such as hexamethylol melamine and dimethylol urea. These cross-linking agents are particularly useful when the cross-linkable resin is an alkyd resin, a polyester resin, an epoxy resin or an acrylic resin. Cellulose resins are another class of resins which may be with the aminoplast resin.

In one embodiment, the aminoplast cross-linking resins are useful in small amounts to cross-link other thermosetting resins such as the water-reducible alkyd resins, water-reducible polyester resins, water-reducible acrylic resins. For example, a useful combination include epoxy resins and cross-linking amine resins.

In simpler systems, the formation of a media is made using an amino resin with formaldehyde, where the formaldehyde is present in either by stoichiometric imbalance or where the formaldehyde is present in an unreacted form or as a sol in the matrix.

Another example is where an amino resin and urea-formaldehyde are cross-linked as above where faster degradation of media is desired for specific host habitats. The urea may also be used as an biolimiting agent and/or nutritional source.

Another media may be formed using acrylic polyols with melamines or isocyanates or combinations with from about 6% to about 18%, or about 12% styrene where the hydroxyl containing monomer is stoichiometricaly adjusted to achieve a biodegradable cross-link in the targeted host habitat.

Polyurethane

In one embodiment, the polymer of the stenoprophiluric media is a polyurethane. The polyurethane resins are those formed by reacting an organic diisocyanate with an active hydrogen-containing material such as polyalkylene ether glycols and hydroxy-terminated polyesters to form isocyanate-terminated polyurethane prepolymers which can be cross-linked or cured with known agents such as compounds having at least two amino nitrogen atoms each having at least one reactive hydrogen atom. Alternatively, the active hydrogen compound, organic diisocyanate and chain extender can be reacted simultaneously to form the desired polymer.

Polyester-urethane resins may be prepared using hydroxy-terminated polyesters which are prepared by polycondensation of an aliphatic dicarboxylic acid and a molar excess of an aliphatic glycol. In another embodiment, the polyester-urethane resins are prepared by ring-opening polymerization of a cyclic ester of the presence of a difunctional compound as an initiator. The polyesters obtainable by polycondensation of one or more of the dicarboxylic acid described herein and one or more of the aliphatic glycols described herein. The resins are exemplified by those obtained by reaction between adipic acid, sebacic acid, maleic acid and other dicarboxylic acids with ethylene-glycol, 1,2-propylene glycol, 1,4-butylene glycol, 1,3-butylene glycol, etc. Examples of the polyesters prepared by polymerization of cyclic esters are those prepared by epsilon-caprolactone, delta-methyl-epsilon-caprolactone and beta-propiolactone in the presence of an initiator such as a glycol, which may include 1,4-butylene glycol, ethylene glycol or diethylene glycol.

The polyalkylene ether urethanes are those prepared by reacting the isocyanates with polymeric polyhydroxy compounds such as those described herein which include polyether polyols, such as polyalkylene ether glycols, polyalkylene arylene ether-thioether glycols and polyalkylene ether triols. The polyalkylene ether glycols and triols are preferred and these include glycols having the formula $HO(RO)_nH$ wherein R is an alkylene radical which need not necessarily be the same in each instance, and n is an integer. Representative glycols include polyethylene ether glycol, polypropylene ether glycol and polytetramethylene ether glycol. Representative polyalkylene ether triols are made by reacting one or more alkylene oxides with one or more low molecular weight aliphatic triols. The alkylene oxides most commonly used have molecular weights between about 44 and 250 and these include ethylene oxide, propylene oxide, butylene oxides, 1,2-epoxybutane and 2,3-epoxybutane. The ethylene, propylene and butylene oxides are particularly useful. The aliphatic triols most commonly used have molecular weights between about 92 and 250. Examples include glycerol, 1,2,6-hexane triol and 1,1,1-trimethylol propane.

Representative examples of the polyalkylene ether triols include: polypropylene ether triol (molecular weight 700) made by reacting 608 parts of 1,2-propylene oxide with 92 parts of glycerin; and polypropylene ether triol (molecular weight 6000) made by reacting 5866 parts of 1,2-propylene oxide with 132 parts of 1,2,6-hexane triol.

Other active hydrogen-containing compounds which can be reacted with polyisocyanates to form urethanes are long-chain polymers containing at least two groups having at least one active hydrogen atom as determined by the Zerewitinoff method. Examples of such compounds include in addition to the polyesters and polymeric polyhydroxy compounds described above, polyamides, polyepoxides, reaction products of phenols and alkylene oxides, formaldehyde resins, hydrogenation products of olefin-carbon monoxide copolymers and polyepihalohydrins.

Polymers which can be employed in the media include oil-free polyester resins, unsaturated polyester resins, alkyd resins, acrylic resins and epoxy resins. The polymers also include urethane resins which form when a di- or polyisocyanate group (—NCO—) bearing intermediate (such as an isocyanate curative) reacts with a di- or polyhydroxyl-bearing species. The species used to react with the isocyanate functionality can be described as any hydrogen donor bearing two or more active hydrogens. Although there is a large array of hydrogen donors for use in the preparation of polyurethane coatings, hydroxyl-based systems are especially useful. Useful hydroxyl-based systems include hydroxylated acrylics, hydroxylated (saturated) polyesters, epoxies and other polyether-based polyols, polycaprolactone-based polyols, castor oil derivatives, and polyamides, phenolics and amino systems. Useful isocyanate-terminated species include the aliphatic species, such as hexamethylene diisocyanate and isophorone diisocyanate and the aromatic species, such as toluene diisocyanate and diphenylmethyl diisocyanate.

In one embodiment, a urethane is linked by isocyanates with zinc metal or copper metal to form a suitable media having maximum durability where abrasion resistance is required. This is a very durable media which is ideal for use on oil platforms and drilling rigs where work boats continually strike structural members at the waterline, the most aggressive fouling zone on a structure which often sees coatings or media abraded or worn off causing a very difficult situation for corrosion and fouling protection of the substrate.

In another embodiment, use is made of an aliphatic isocyanate cross-linked polyol (urethane) where pre-reactions or pre-polymers or adducts are used to change the degradation rate of the final cure media thus the bioavailability of the agent.

A strong although costly marine media is one made of urethane which is made by carefully managing the moisture in the curing process whereby the water is permitted to be excluded under tightly controlled reaction staging where the final amount of water in the media succinctly determines the degradation rate particularly through hydrolysis.

Acrylic Resin

In another embodiment, the polymer of the stenoprophiluric media is an acrylic resin. The acrylic resins are obtained by polymerizing a suitable combination of a functional group-containing monomer and another copolymerizable monomer in an ordinary manner. The polymerization temperature is ordinarily between about 60° C. and about 100° C., and polymerization time is usually within a range of about 0.5 hours to about 15 hours, or about 1 hour to about 12 hours, or about 3 hours to about 10 hours. Examples of the functional group-containing monomers include hydroxyl group-containing monomers, such as beta-hydroxyethyethyl acrylate, beta-hydroxypropyl acrylate, beta-hydroxyethyl methacrylate, beta-hydroxypropyl methacrylate, N-methylol acrylamide and N-methylol methacrylamide; carboxyl group-containing monomers such as acrylic acid, methacrylic acid, itaconic acid, maleic acid, fumaric acid, as well as monoesters of maleic acid and fumaric acid with monoalcohols; alkoxyl group-containing monomers such as N-butoxy-methylmethacrylamide and N-butoxymethylacrylamide; and epoxy group-containing monomers such as glycidyl methacrylate, glycidyl acrylate and allyl glycidyl ether. These monomers may be used either alone or in combination of two or more therof. The functional group-containing monomer is used in an amount of about 5 to about 40% by weight of total monomers.

Examples of the monomers copolymerized with these functional group-containing monomers include olefinically unsaturated monomers such as ethylene propylene and isobutylene; aromatic monomers such as styrene, vinyltoluene and alphamethylstyrene; esters of methacrylic acid and alcohols of 1 to about 18 carbon atoms such as methylmethacrylate, ethylmethacrylate, propylmethacrylate, n-butylmethacrylate, isobutylmethacrylate, cyclohexylmethacrylate, 2-ethylhexylmethacrylate and laurylmethacrylate; vinyl esters of carboxylic acid of about 1 to about 11 carbon atoms such as vinyl acetate, vinyl propionate and vinyl 2-ethylhexylic acid; as well as vinyl chloride, acrylonitrile and methacrylonitrile. They may be used either alone or in the form of a mixture of two or more of them. Commercial examples of useful acrylic resins include Carboset CR-785, a styrene-acrylic emulsion from B. F. Goodrich; Resin XC-4005, a water-reducible acrylic from American Cyanamid; etc.

Alkyd Resin

In another embodiment, the stenoprophiluric media includes an alkyd resin. The alkyd resins are obtained by reacting a dihydric or polyhydric alcohol and a polybasic acid or anhydride in the presence of a drying oil using known techniques. The polyhydric compounds and polybasic acids may be any of those described herein. Examples of the dihydric or polyhydric alcohols include glycerol, pentaerythritol, sorbitol and diethylene glycol. Examples of the polybasic acids or anhydrides include phthalic acid, isophthalic acid, maleic anhydride, fumaric anhydride, non-conjugated linoleic acid, oleic acid, adipic acid, azelaic acid, sebacic acid, tetrachlorophthalic anhydride, and chlorendic anhydride. Examples of the drying oils include soybean oil, linseed oil, dehydrated castor oil, non-oxidizing castor and coconut oils, tung oil, fish oil, sunflower oil, walnut oil, safflower seed oil and tall oil. These alkyd resins may be produced, for example, by direct fusion of glycerol, phthalic an hydride and drying oil at a temperature in the range from about 210° C. to about 235° C. Solvents are then added to adjust the solids content. The amount of drying oil varies depending on the intended use. With respect to the high solids compositions of the invention, the level of drying oil is preferably minimized.

In one embodiment, the polymer is an alkyd resin of esterfied mixtures of dibasic acids, polyols, and fatty acids where glycerine, pentaerythritol or trimethylo propanone are utilized as a basis for a media. In another embodiment, the media is formed by using an alkyd resin of the dibasic acid phthalic anhydride with a zinc particulate. The media may also be an alkyd resin which is modified by the use of isophthalic acid alone or in combination with terephthalic acid. In another embodiment, the alkyd resin uses a terephthalic acid for increased stability. In one embodiment, the media is prepared with an alkyd resin such as a polyester, chain stopped with fatty acids.

In another embodiment, a traditional alkyd resin is used in conjunction with an epoxy or other resin systems described herein. These are useful for hydrophytic environments as well as in standard aqueous habitats. In one embodiment, an alkyd resin which contains benzoic acid as a chain stopper is used to form the media.

Polyester

The polyester resin is typically the condensation product of a polycarboxylic acid or its derivative (anhydrides, $C_{1-8}$ alkyl esters, etc.) and a polyhydric alcohol. The polyester resin usually encompasses from about 50% to about 95%, or preferably from about 55% to about 90%, or more preferably from about 60% to about 85% by weight of the unsaturated polyester resin system. In one embodiment, the polyester resin has lower acid numbers, such as less than about 30, with about 20 or less being preferred, have good spraying properties in applications where the unsaturated polyester resin system is applied by spraying. In another embodiment, the polyester has a narrow molecular weight distribution (Mw/Mn). The molecular weight distribution is typically from about 2 to about 8, or preferably from about 2.5 to about 5. In one embodiment, the polyester resin is free of dicyclopentadiene olefins, alcohols or acids.

The polyhydric alcohols used to prepare the polyester typically have from about 4 to about 12, preferably from about 4 to about 8 carbon atoms. In one embodiment, the polyhydric alcohols have a neo structure, e.g., a carbon atom bonded solely to other carbon atoms. Examples of the polyhydric alcohols are listed herein and include glycerol, pentaerythritol, dipentaerythritol, tripentaerythritol, trimethylolethane, trimethylolpropane, and di-trimethylolpropane.

In one embodiment, the polyester resin is prepared with a transesterification catalyst. The catalyst is present in an amount from about 0.05% to about 2% by weight. Transesterification catalysts include metal-containing catalysts, metal glycoxides, such as antimony glycoxide; alkali metal borohydrides, such as sodium borohydride, potassium borohydride, magnesium borohydride, calcium borohydride, aluminum borohydride, titanium borohydride, and tin borohydride; metal oxides, such as beryllium oxide, magnesium oxide, antimony trioxide, tin(IV) oxide, and dibutyltin oxide; metal hydroxides, such as magnesium hydroxide, metal acetates such as magnesium acetate, manganese acetate, tin(IV) acetate, metal carbonates, such as lithium carbonate, sodium carbonate, potassium carbonate, magnesium carbonate, tin(IV) carbonate, tetraalkyl metals, such as tetraalkyl titanate, such as tetraisopropyl titanate, tetra-n-butyl titanate, and tetrakis (2-ethylhexyl) titanate, and tetraalkyl zirconate, such tetraisopropyl zirconate, tetra-n-butyl zirconate, tetrakis (2-ethylhexyl) zirconate; and metal nitrates, such as tin(IV) nitrate. Other suitable transesterification catalysts include, for example, Bronsted acids such as sulfuric acid and Lewis acids such as aluminum triisopropoxide. Preferred transesterification catalysts are antimony glycoxide, $(Sb_2(OCH_2CH_2O)_3)$, and manganese acetate in about equal portions.

In another embodiment, the polyester resin is prepared using a reaction product of a polyol and a fatty carboxylic acid. The reaction product may contain an average of two, three or more, preferably two, residual hydroxyl groups which may be used in the preparation of the polyester resin. Residual hydroxyl groups are those remaining after the reaction of the polyol and the fatty acid. The residual hydroxyl groups are reacted in preparing the unsaturated polyester systems. The polyols include those which have three or more hydroxyl groups, such as those listed herein, and have from about three to about 12, or from about 3 to about 8 carbon atoms. The fatty acids include those having from about 8 to about 30, or from about 12 to about 24, or from about 14 to about 22 carbon atoms. Examples of fatty acids include dodecanoic acid, hexadecanoic acid, stearic acid, palmitic acid, oleic acid, etc. The preferred reaction products are glycerol based, such as glycerol monostearate. In one embodiment, the fatty acids are saturated fatty acids.

In another embodiment, the polyester resin may be prepared from at least one fatty reactant selected from the group consisting of a fatty primary alcohol, a fatty epoxide, a fatty monocarboxylic acid and mixtures thereof, wherein each member of the group has up to about 100 carbon atoms. In one embodiment, these materials contain from about 12 to about 90, or from about 25 to about 80 carbon atoms. In one embodiment, these materials are saturated. Examples of fatty alcohols include oleyl alcohol, lauryl alcohol, stearyl alcohol, UNILIN 425 (a $C_{30}$ avg. linear primary alcohol), UNILIN 550 (a $C_{40}$ avg. linear primary alcohol), and UNILIN 700 (a $C_{50}$ avg. primary alcohol). UNILIN alcohols are available from Petrolite Corporation. The fatty epoxides include epoxidized fatty alcohols, such as oleyl epoxide, stearyl epoxide, epoxidized soybean oil, epoxidized linseed oil, epoxidized $C_{8-50}$ alpha-olefins, etc.

The carboxylic acids and their derivatives used to prepare the polyester are typically dibasic unsaturated, preferably alpha, beta-olefinically unsaturated, carboxylic acids or their derivatives. Examples of these carboxylic acid and their derivatives include maleic acid, fumaric acid, chloromaleic acid, itaconic acid, citraconic acid, methyleneglutaric acid and mesaconic acid and their esters or preferably their anhydrides, as well as succinic acid, glutaric acid, d-methylglutaric acid, adipic acid, sebacic acid, pimelic acid, phthalic anhydride, o-phthalic acid, isophthalic acid, terephthalic acid, dihydrophthalic acid, tetrahydrophthalic acid, tetrachlorophthalic acid, dodecanedicarboxylic acids, nadic anhydride, cis-5-norbornene-2,3-dicarboxylic acid or anhydride, dimethyl-2,6-naphthenic dicarboxylate, dimethyl-2,6-naphthenic dicarboxylic acid, naphthenic dicarboxylic acid or anhydride and 1,4-cyclohexane dicarboxylic acid. Monobasic, tribasic or higher polybasic carboxylic acids, for example ethylhexanoic acid, methacrylic acid, propionic acid, benzoic acid, 1,2,4-benzenetricarboxylic acid or 1,2,4,5-benzenetetracarboxylic acid may also be used in preparing the polyester resins.

In one embodiment, the carboxylic acids and their derivatives are the combination of a non-aromatic carboxylic acid or derivative and an aromatic carboxylic acid or derivative. Examples of the various acids and their derivatives are disclosed herein. In one embodiment, the non-aromatic acid is typically present in an amount from about 40% to about 70%, or from about 40% to about 65%, or from about 45% to about 60% by mole of non-aromatic carboxylic acid or derivative. These carboxylic acids typically have from about 3 to about 12, or from about 3 to about 8, or from about 4 to about 6 carbon atoms. Useful acids or derivatives are maleic or fumaric acids or esters and maleic anhydride. In another embodiment, the aromatic carboxylic acids or their derivatives are generally present in an amount from about 30% to about 60% by mole, or from about 35% to about 60%, or from about 40% to about 55% by mole. The aromatic carboxylic acid or their derivatives have from about 8 to about 18, preferably from about 8 to about 12 carbon atoms. The aromatic carboxylic acids and their derivatives are disclosed herein. The aromatic carboxylic acids and derivatives are disclosed herein and useful aromatic carboxylic acid and derivatives, include phthalic anhydride, o-phthalic acid, iso-phthalic acid, etc.

As described above the polyester resin is prepared from polyhydric alcohols, preferably glycols. Suitable polyhydric alcohols include alkanediols and oxa-alkanediols, for example, ethyleneglycol, 1,2-propyleneglycol, propane-3-diol, 1,3-butyleneglycol, butene-1,4-diol, hexane-1,6-diol, 2,2-dimethylpropane-1,3-diol, diethyleneglycol, triethyleneglycol, polyethyleneglycol, cyclohexane-1,2-diol, 2,2-bis-(p-hydroxycyclohexyl)-propane, butene-1,4-diol, 5-norbornene-2,2-dimethylol, 2,3-norbornene diol, and cyclohexane dimethanol.

In one embodiment, the polyhydric alcohols are neopentyl glycol and propyleneglycol. The polyester resin is generally prepared from polyhydric alcohols where from about 45% to about 70%, or from about 50% to about 65% by mole of the polyhydric alcohols are those having a neo structure. Examples of such alcohols include neopentylglycol, dimethylpropane-1,3-diol, 2,2-dimethylheptanediol, 2,2-dimethyloctanediol, 2,2-dimethyl-1,3-propanediol, pentaerythritol, dipentaerythritol, tripentaerythritol, trimethylolpropane, di-trimethylolpropane, 2,2,4-trimethyl-1,3-pentanediol, 2-butyl-2-ethyl-1,3-propanediol, 3-hydroxy-2,2-dimethylpropyl 3-hydroxy-2,2-dimethyl propanate, etc.

In another embodiment, the unsaturated polyester is prepared from alcohols having a neo structure. In this embodiment, greater than 80%, or greater than 90% by mole or all of the polyhydric alcohols have a neo structure. Examples of neo structure containing a polyhydric alcohols are discussed herein.

In one embodiment, the polyester is a conventional unsaturated polyester, which are those available commercially and which contain reactive diluent. They are prepared from one or more of the above polycarboxylic acids or derivatives and one or more of the above polyhydric alcohols. In one embodiment, the conventional polyester is prepared from a combination of a non-aromatic and an aromatic carboxylic acid or derivative thereof, preferably phthalic acid and maleic anhydride. The polyol is typically neopentylglycol and propyleneglycol. The conventional polyester generally contains from about 20% to about 45% or preferably from about 30 to 38% reactive diluent such as those described above. The unsaturated polyester resin is typically present in an amount from about 55% to about 85%. Commercial polyester resins are available as ortho or iso polyester from many companies. Examples of these companies include Reichold Chemical, Ashland Chemical, Huls AG, and Alpha Resin.

In order to improve the abrasion resistance of urethane alkyds in heavy duty industrial applications and to moderate the hydrolysis resistance, a portion or all of the dibasic acid of the alkyd resin is replaced with a di-isocyanate (TDI).

Unsaturated polyester resins with maleates and/or fumarates in their backbone make excellent media yielding sites for free radicals which can manage higher levels of occlusions. In another embodiment, styrene with a peroxide initiator is reacted with the polyester.

In another embodiment, the media is formed using an alkyd resin which is prepared by heating mono-glyceride process oils and fatty acids, additional glycerine or other polyols, such as those described herein, in the presence of a transesterfication catalyst. An example of the transesterification catalyst is tetraisopropyl titanate. The reaction mixture is heated to about 230–250° C. Phthalic anhydride is then added to the reaction. Xylene may be used to azeotropically remove water.

In one embodiment, fatty acid is used to prepare a glycerine free alkyd resin media. The resin is prepared from fatty acids, dibasic acids and polyols. In one embodiment, the reaction is not carried to completion to provide for biodegradation.

In one embodiment, the media is formed with polymers and oligomers of unsaturated polyester resins containing two or more methacrylate or acrylate groups per polymer chain with an epoxide functional resin with methacrylic acids or a functional isocyanate or hydroxyl functional methacrylate monomer to yield a radiation cured media with unique capabilities in engineered products where standard application techniques are not practical.

Among the polyesters which are useful in the stenoprophiluric media are polyesters of aromatic dibasic acids and alkylene glycols. The polyesters also may be derived from a mixture of aromatic dicarboxylic acids containing at least some symmetrical aromatic dicarboxylic acid, one or more acyclic dicarboxylic acids, and one or more diols. Examples of symmetrical aromatic dicarboxylic acids include terephthalic acid, dibenzoic acid, ethylene bis-p-oxy benzoic acid, tetramethylene bis-p-oxy benzoic acid, and 2,6-naphthalic acid. Other aromatic dicarboxylic acids which can be used in conjunction with the symmetrical dicarboxylic acid include o-phthalic, isophthalic acid, etc.

The glycols which are reacted with the dibasic acids to form the polyesters are glycols represented by the formula HO(Y)OH (II) wherein Y is an alkylene group containing from about 2 to about 10, or 2 to about 6, or 2 to about 4 carbon atoms. Examples of such glycols include ethylene glycol, 1,2- and 1,3-propanediol, 1,4-butanediol, neopentyl glycol, 1,6-hexanediol, polyethylene glycol, etc. Representative of the acyclic dicarboxylic acids which can be incorporated into the polyesters are those characterized by the formula HOOCCH$_2$XCH$_2$COOH (III) wherein X is a linear chain composed from 2 to about 8 carbon atoms. In one embodiment, mixtures of two or more acyclic dicarboxylic acids are utilized, and the acyclic dicarboxylic acids in the mixture will differ from each other by at least 3 carbon atoms in the linear chain. Specific examples of the acyclic dicarboxylic acids represented by the above Formula III include adipic acid, pimelic acid, suberic acid, azelaic acid, oxy-dibutyric acid, sebacic acid, 5-oxa-1,10-decanedioic acid, 4-n-propyl suberic acid, dodecane dioic acid, tridecane dioic acid, etc. The useful polyesters include those prepared from: terephthalic acid, azelaic acid and pentamethyleneglycol; terephthalic acid, isophthalic acid and adipic acid; terephthalic acid, isophthalic acid, adipic acid and sebacic acid; terephthalic acid, isophthalic acid, adipic acid and ethylene glycol; etc. Copolyesters of such mixtures can be prepared by known techniques, and they may be prepared directly from the above-identified dicarboxylic acids, or the copolyesters can be prepared from the lower alkyl esters of said dicarboxylic acids such as dimethyl terephthalate, dimethyl isophthalate, dimethyl sebacate, dimethyl adibate, etc. Procedures for preparing copolyesters are described in, for example, U.S. Pat. No. 2,623,033 (Snyder) and U.S. Pat. No. 2,892,747 (Dye), both of which are hereby incorporated by reference for their disclosure of linear copolyesters derived at least in part from symmetrical aromatic dicarboxylic acids.

In one embodiment, the resins are cross-linkable thermoplastic polyesters. Particularly useful are linear saturated polyester resins containing hydroxyl groups. The linear saturated polyester resins may be characterized by a hydroxy number from about 5 to about 60 and more generally by a hydroxyl number from about 5 to about 15. The molecular weight of the linear saturated polyester resins range from about 5000 to about 50,000 or more. Linear polyester resins having a hydroxyl number from about 5 to about 15 and a molecular weight from about 10,000 to about 20,000 are useful in this invention. The linear polyesters generally may be derived from a mixture of aromatic dicarboxylic acids and a mixture of glycols. The aromatic dicarboxylic acids are described herein and include terephthalic acid, dibenzoic acid, ethylene bis-p-oxy-benzoic acid, 2,6-naphthalic acid, orthophthalic acid, isophthalic acid, etc. Mixtures of terephthalic and isophthalic acids are particularly useful. The glycols are described herein and include ethylene glycol, 1,2- and 1,3-propanediol, 1,4-butanediol, neopentyl glycol, 1,6-hexanediol, etc. A particularly useful mixture is a mixture of ethylene glycol and neopentyl glycol.

A particularly useful linear polyester containing hydroxyl groups is derived from a mixture of terephthalic acid, isophthalic acid, ethylene glycol and neopentyl glycol. The relative amounts of the four components may be varied over a wide range. For example, the polyester resin can be derived from mixtures comprising from about 20 to about 60 mole percent of terephthalic acid, from about 15 to about 50 mole percent of isophthalic acid, and from 10 to about 50 mole percent of the glycol mixture. One such group of polyester resins are available commercially from the Nobel Dynamit Company under the general trade designation Dynapol®. These high molecular weight linear saturated polyesters are characterized as having a hydroxyl number from about 5 to about 60 and molecular weights from about 3000 to about 18,000. Specific examples include Dynapol L205, characterized as having a molecular weight of 15,000 and a hydroxyl number of 10; Dynapol L206, having a molecular weight of 18,000 and a hydroxyl number of 8; and Dynapol LH812, having a molecular weight of about 3000 and a hydroxyl number of 35.

In one embodiment, a variety of cross-linking materials may be utilized with the polyesters, and these include, for example, aminoplasts (amino resins), e.g., urea formaldehyde and melamine formaldehyde and their alkoxy derivatives, phenol formaldehyde resins, epoxy resins, isocyanates, etc. Examples of useful isocyanate cross-linking agents include toluene diisocyanate (TDI), 4,4'-methylene-bis(diphenyl) diisocyanate, a 2:1 molar adduct of toluene diisocyanate and diethylene glycol, 1,6-hexamethylene diisocyanate, adducts of toluene diisocyanate and trimethylol propane, etc. The polyisocyanates used as cross-linkers may be blocked with thermally unstable blocking agents such as phenols, alcohols, etc. The weight ratio of polyester/cross-linker in the compositions of the invention may be varied between about 95/5 to about 60/40 or even less.

In one embodiment, the polyesters used in combination with the epoxy resins are linear polyesters of aromatic dibasic acids and alkylene glycols. Generally, these polyesters are derived from a mixture of aromatic dibasic acids described herein, such as terephthalic and isophthalic acid with an alkylene glycol containing from 2 to about 6, or 8 carbon atoms in the alkylene group. The glycols are described herein and include ethylene glycol, trimethylene glycol, 1,4-butylene glycol, etc. In addition to the aromatic dicarboxylic acids and the alkylene glycol, the reaction mixture also may contain an acyclic dicarboxylic acid. The relative amounts of aromatic dicarboxylic acid and a cyclic dicarboxylic acid may be varied in order to obtain polyesters having different characteristics. In general, the ratio of equivalents of aromatic dicarboxylic acids to acyclic dicarboxylic acid will be from about 2:1 to about 1:2 and more generally about 1:1. The ratio of dicarboxylic acid to glycol also may be varied, and the glycol is generally present in excess amounts. Thus, ratios of dicarboxylic acids to diol generally are from about 1:1 to about 1:2. The reaction between the dicarboxylic acid mixture and the diol generally is effected by heating the mixture to an elevated temperature in the presence of catalysts. Tin catalysts are especially useful for such purposes, and examples include dibutyl tin oxide and dibutyl tin dilaurate. Other catalysts which may be utilized include antimony oxide. The polyesters and copolyesters prepared in this manner generally will have molecular weights from about 5000 to about 50,000 and will be further characterized as having hydroxyl numbers between about 5 and 15.

Phenolic Resin

In another embodiment, the stenoprophiluric media includes a phenolic resin. The phenolic resins are any of the several types of synthetic thermosetting resins made by reacting a phenol with an aldehyde. Examples of phenols include phenol, cresols, xylenols, p-t-butyl phenol, p-phenyl phenol, bis-phenols and resorcinol. Examples of the aldehydes include formaldehyde, acetaldehyde and furfural. Phenol-formaldehyde resins are a preferred class of such phenolic resins.

A phenolic resin where stoichiometry is adjusted to permit biodegradation at such a rate as will permit very low concentrations of highly biolimiting agents can be considered, as in a closed system where anaerobic conditions may exist and no potential exists for release of the agent to the environment.

Halogenated Polyolefins

The polymers of the stenoprophiluric media may also be halogenated polyolefins, such as chlorinated polyethylene, chlorinated polypropylene, mixtures of chlorinated polyethylene and chlorinated polyolefin, etc. Chlorosulfonated polyolefins, such as chlorosulfonated polyethylene and chlorosulfonated polypropylene also may be utilized. Examples of chlorinated polyolefins include the chlorinated polyolefins available from Eastman Chemical Products, Inc. under the designations CP-343-1 and CP-343-3 which are chlorinated polyolefins in various concentrations of xylene including solutions containing 40% and 50% of the chlorinated polyolefins in xylene. Commercially available chlorosulfonated polyethylenes are available from the DuPont Company under the general trade designation Hypalon Synthetic Rubber.

Chlorosulfonated olefins such as chlorosulfonated polyethylene are derived from the reaction of a mixture of chlorine and sulfur dioxide on any of the various polyethylenes. The product of this reaction is a chemically modified form of the original polyethylene, and the product may contain from 20% to about 40% chlorine and about 1% to 2% sulfur present mostly as secondary sulfonyl chloride groups ($SRR'CHSO_2$ Cl) wherein R and $R^1$ are independently alkyl groups with 1 to about 6 carbon atoms, e.g., methylene, ethylene, propylene, and butylene. The sulfonyl chloride groups are available as cross-linking or curing sites.

A number of chlorine containing vinyl-acrylic emulsions are available from ICI Resins which include emulsions containing three polymers, namely, polyvinylidene chloride/polyvinyl chloride/polyacrylic acid under the general trade designation "Haloflex". For example, Haloflex HA-202 is such a mixture containing 60% solids and 64% chlorine, and Haloflex EP-252 contains 55% solids and 38% chlorine.

Mixtures of one or more of the above-described resins may be used with advantage. For example, mixtures of epoxy resins and amino resins are useful, and the amino resin may serve as a cross-linking resin.

A variety of cross-linking resins can be utilized in the aqueous compositions of the invention, and these include, for example, aminoplast resins, urethane resins, acrylic resins, epoxy resins, alkyd resins, phenol-formaldehyde resins, etc., and mixtures thereof.

Silicone Polymers

In one embodiment, the polymer of the media is a silicone polymer. The silicone polymers include those polymers formed utilizing silicone, siloxanes, including silanol and other silica derived compounds. Silicone polymers based on silanol groups can be made useful as a media under acidic or basic conditions. Organic polymers or monomers may be blended to achieve desired properties for a targeted host habitat. The features of the organic polymer would be utilized with the added resiliency of the silicone, much like a composite gains strength or attributes from each of its components.

Silica Media

In another embodiment, the media comprises a silcone jelly. Silicone jellies may form composites or amalgamated media with occlusions physically mixed or dispersed. These applications can withstand very little abrasion contact but retain the unique ability to withstand high temperature or severe host habitat environments. One such use would be in a chemical reactor system or a fuel pipeline system used for transporting fuels and oils and/or lubricants. Another application for these amalgams, which could also be cosmolene, would be in fuel storage systems for diesel, bunker or jet fuel. A secondary benefit may be in the ability of a formed biomass to produce allelochemicals which in effect would keep the fuel or oil from biodegrading, an ongoing problem with fuel storage. Additionally allelochemicals from one micro-habitat could be extracted and used in fuels as a bio-guard agent.

Where improvements in coating performance or media enhancement to achieve stenoprophiluric properties are desired, silicone intermediates designed to react with hydroxyl groups on an alkyd resin, or intermediates with silanol groups or with silyethers such as Si-OMe-titanate catalysts, promote the reaction of polyol and prevent condensation.

A totally inorganic binder for a media may be prepared using tetraethylorthosilicate and cured with water from the environment or other source. Two moles of water in theory liberate four moles of ethanol and build a complex three dimensional silica network by way of silanol-containing intermediates. Interspersions of nutrients, agents, and additives provides a novel structure for stenoprophiluric activity by very specialized silica based organisms as well as traditional naturally occurring more widely diverse types.

Additionally, totally inorganic silica binder media can be pigmented with high levels of zinc, copper, vanadium, or other metals or organometalics which have specific agent demands in unique host habitats. In some closed loop water system or peculiar pass-through water systems, non-indigenous species may be introduced. This media permits very well articulated placement of highly biolimiting agents in those type of environments.

In the case of such a media where zinc in the primary or single agent, an additional benefit can be derived through the use of the form and presence of zinc which may eliminate the use of an intermediate or base coat or mid coat which may be a sacrificial pigment on a steel substrate to provide for electrodeposition and improved adhesion of a three coat stenoprophiluric system where not only isolation of the resulting micro-habitat is achieved to maintain the integrity of the unique consortium of organisms, but the substrate is stabilized as well, preventing the dissolution of the substrate which could significantly change the ability of the intended consortium to survive.

A non-VOC or solvent less media may be produced from a trialkoxysilyl group (Si(OR)$_3$) which is capable of being hydrolyzed by water and self condensing to form a crosslinked network suitable for stenoprophiluricity. Platinum and other precious metals and other specialty catalysts may additionally be used as agents. This may include silver, gold, rubidium, gallium and many other elements. In another embodiment, the metals are present as colloidal metal dispersions and these dispersions may include the additives described herein.

The use of trimethyloxysiylpropyl group and an amine epoxide or other such functional group which can be moisture cured to make a media as a cross over of physical and chemical properties of a matrix in media formation can be made. This also adds excellent adhesion properties, such that a media can be attached to a glass(y) substrate.

Lacquer

In another embodiment, the media comprises a solvent-borne lacquer. The lacquers include lacquers but not limited to; cellulose derivatives, acrylic lacquers, and halogenated lacquer resins. In naturally occurring substances which form excellent media, cellulose polysaccharide lacquers may be used which may use cellulose acetate butyrate (CAB) with an addition of either aluminum compounds or titanium compounds at the bioactive limits for an applied micro-habitat. In one embodiment, the media contains a natural polysaccharide polymer cellulose, which is derived from cotton linters or wood pulp. Cellulose resins include cellulose esters including nitrocellulose, carboxylic esters of cellulose, such as cellulose acetate, and cellulose ethers, such as hydroxyethyl cellulose. Nitrocellulose is made by nitrating cellulose with a mixture of nitric and sulfuric acids in the presence of water. Nitrocellulose lacquers are formulated by suitable blending of nitrocellulose resins and solvents. Base nitrocellulose resin is generally blended with other resins and plasticizers to give satisfactory compositions. Nitrocellulose has good compatibility with other resin systems. Thus, acrylics, phenolics, vinyls, epoxies, natural resins, amino resins and alkyds are used to upgrade performance and durability of nitrocellulose.

In another embodiment, the polymer of the media is a waterborne thermoplastic coating. These waterborne thermoplastic coatings include but are not limited to; acrylics, latexes, vinyl ester latexes and polyurethane dispersions.

Another specialized media can be prepared using acetoacetate cross-linking reactions, enamine cross-links, Michael reactions of a nucleophile to a vinyl compound making a Michael acceptor; and often an acrylate group in thermo-setting material media applications. Primary amines are often used in a Michael reaction as well. Aziridines, the nitrogen analog top epoxides may also be used when a nitrogen food source as a nutrient or agent is desired as well. Polycarbodiimides can be used to cross-link latexes and water borne dispersions as well.

Another stoichiometric managed media can be achieved for use in extreme or severe habitats where a polyester polyol and diols are kept balanced with polyether polyols which are incorporated for enhanced degradation primarily assisted in high light areas where UV effects are involved from high sunlight.

Amalgam

In one embodiment, the stenoprophiluric media contains an amalgam. An amalgam is a media composite predominately derived from naturally occurring substances, often formed from resins, tars, pitch, gums and included in a mixture with bio-active agents, composites, nutrients, or polymers. Examples include amber, agar, pine tar, pine tree resin, fats, oils, petroleum jellies, waxes, silicone jellies, and gelatins. The media is primarily bound by physical and viscosity is characteristics often related to agglomeration at a temperature forming a solid or semi-solid under the ambient temperature of the host habitat.

In one embodiment, the amalgam is the media which comprises the fatty acids which are oxidized in formation under very irregular orders of bonding and polymerization. This media is classified as an amalgam with the appropriate biodegradation rate after cure.

Composite

In one embodiment, the media is a composite. The composite is the combination of two or more substances which retain their identity while contributing desirable properties to the end product. A material or materials system composed of a mixture or combination of two or more microconstituents or macro-constituents that differ in form and chemical composition and that are essentially insoluble in each other. Examples of composites include polymers filled with fibers, glasses as fibers or pieces as in reinforced fiberglass, pozzolans or quick lime composites such as cements and concretes which form composites with aggregates, cementitious aggregates using zinc particulates, slags, portland cement, polymers, and reinforcement articles, and ceramics (inorganic, non-metallic solids processed or used at high temperature) which comprise fired or baked materials with or without occlusions and composites, to form matrices or structures with desirable physical properties, wood composites, recycled plastic or polymer composites formed by heat and or pressure, asphalts which are filled with aggregate and solvents usually oils, and combinations thereof. Pozzolanic activity is the basic mechanism of forming concrete or cementitious composites utilizing mineral admixtures, hydraulic or pozzolanic reactions of cement and water and additives, often with significant occlusions.

Biolimiting Agent

A biolimiting agent is a substance, compound, element, or molecular complex which has a specified bioactive property. The property changes not only with molecule type but also with concentration. Certain agents are almost always totally toxic to biological life forms while other agents such as silica are tolerated in very high concentrations. The biolimiting agent is in a form that is bio-available, i.e., to provide a biolimiting effect. A highly oxidized or bound form such as a carbonate renders a metal insoluble, i.e., copper.

The bio-supportive matrix also includes a bio-limiting agent. The limiting agent may be present in any amount sufficient to limit the diversity of organism(s) and subsequently to prevent the inclusion of undesired biological organism(s) in the micro-habitat. The bio-limiting agent may be present in an amount considered as little as ultra-trace (part per trillion, such as tin) to as much as that amount considered as a major component (nutrient) relative to the bio-limiting action sought.

In one embodiment, the bio-limiting agent is present in an amount of at least 2%, or at least about 5%, or at least about 10% by weight. The bio-limiting agent is present in an amount up to about 80%, or up to about 70%, or up to about 60% by weight. In some cases part per million concentrations of specific chemicals can account for limiting biological activity. In one embodiment, the biolimiting agent is not bound within the media and, in another embodiment, the biolimiting agent is not oxidized. In another embodiment, the biolimiting agent forms a complex with the excess polarity of the media. The interaction of the biolimiting agent and the media may actually improve the solubility of the biolimiting agent in the environment. For instance, when a copper biolimiting agent is used with a media that has excess amine polarity, then an interaction, which is believed to be a complex, occurs that makes the copper biolimiting agent more soluble in water, especially salt water.

Examples of bio-limiting agents include heavy metals: lead, vanadium, molybdenum, nickel, tin, copper, mercury, etc. and alloys of those metals. The bio-limiting agents may be metal containing organic compounds such as organo-metallics of the aforementioned metals and their alloys. For instance tin or copper compounds may be used as bio-limiting agents, often referred to as co-polymeric active ingredients. Additionally, metal-free bio-limiting agents may be used. Examples of metal-free bio-limiting agents include organic biocides such as isothiazolone, phenol compounds, such as coal tars, thiadiazole compounds, thiocarbamate compounds, etc. Bio-limiting agents may also be inorganic/organic compounds such as tri-butyltin. Any bio-limiting agent which assists in creating a modified or adapted biomass due to a new, or non-natural habitat or environment can be used.

The present invention incorporates a dispersion of a biolimiting agent in the media. This available concentration creates a surficial contact concentration usually measured in micro-grams per square centimeter per day which as available at the interface of the media and the habitat limits the selection of species, numbers, and kinds which will establish a sub-habitat or micro-habitat. These agents can be from the media constituents themselves by design. They can be introduced agents or occlusions to the matrix of the media for their specific biolimiting purposes. The agents can also be formulated from the additives used in coatings and paints and polymers to achieve certain properties of hardness, formation of matrix control, or additives which provide specific mechanical, physical, or chemical properties. In the case of occlusions the use of a metal such as copper or manganese or iron instead of an oxide form, in a preferential size and shape, may provide a much different level of availability and change the amount of the agent available on a time and unit surface area basis.

Bio-limiting agents include elements like mercury, and compounds like cyanide or DDT. Trace levels of an agent may be a required nutrient for one organism yet be present at a concentration which is toxic to another organism. Another species may be tolerant of a given amount, another may find it toxic at the same amount, still another may require it as a necessary nutrient, others may require the specific amount to manufacture secondary metabolites or allelochemicals. While copper is a nutrient in ionic or simple oxidized form, it is insoluble and not available to biological use when the copper is bound in the form of copper carbonate. Additional examples of biolimiting agents include zinc, PCB, CN, Mn, DDT, Taxol, Bryostatin, pesticides, herbicides, organometalics, metals, oxygen, chlorine, iron, copper, chromium, cadmium, arsenic, lead, and most pesticides and herbicides including thiazalone, DDT, and Malathion. Additionally, organo-metallics such as organo-tins find extensive commercial use. Alloys such as copper-nickel, stainless steels and zinc compounds such as zinc omadine may also be used.

Where the media contains an agent which is a salt of lead, zirconium, tin, molybdenum, vanadium, titanium, chromium, cadmium, columbium, niobium, iron, manganese, magnesium, sodium, arsenic, independently or in the presence of synergistic modifiers of bioactivity and chemical activity including the above and calcium, silica, manganese, or cobalt as elements or compounds. These agents are used at an extremely low concentration and are meant as sub-molecular agents and designed not to be released into the environment in an unbound form.

The literature, both scientific and popular, abounds with confusion on the effects and definitions of biolimiting agents. Tolerance and toxicity are often confused as one in the same. Concentration expressed as milligrams per liter (mg/l) of solution are confused with the orders of magnitude smaller measure of micro-grams per square centimeter per day ($\mu g/cm^2/day$). Additionally, the same concentration of a substance while being an essential nutrient for one organism may be lethal to another. Lastly, organisms are affected by the form of the substance and the rate at which it may be metabolized, absorbed through a membrane, or reacted.

In one embodiment, the biolimiting agent is a spherical or cuboidal shape. In another embodiment, the biolimiting agent has surface area from from about 0.2 to about 1.5, or from about 0.4 to about 1.2, or about 0.8 $m^2/g$. In another embodiment, the biolimiting agent has a bulk density of about 1.5 to about 6, or from about 2 to about 5, or from about 2.5 to about 4, or about 3.2 g/ml. In another embodiment, the average particle size is from about 10 to about 60, or from about 15 to about 50, or from about 20 to about 40, or 29 microns.

While the following discussion relates to copper, the present invention in not limited to copper and applies to all agents both organic and inorganic. Many of the mechanisms discussed with copper can be applied to the other substances. Variances occur due to the ability of the substance to react chemically with regard to organisms and the inorganic environment. When examining any data concerning toxic concentrations, the state of the substance and the effect of organics and particulates in the micro-habitat of which they are being reviewed must be considered. For example, phosphate presence reduces effects of copper on *Saccharomyces carlbergensis,* while under manganese deficiency. It has been demonstrated that copper will inhibit several dinoflagelates until organic chelation occurs which then lessens the copper effect and permits organisms like *Gonyaulax tamarensis* to successfully compete with other phytoplankton in coastal waters.

Cupric ion may be toxic to many microbial life forms in sufficient concentration, while at the same time, the concentration and form of copper has been shown to determine the species succession in diatoms. Copper has also been shown to affect dominance and diversity of other algae as well. Persistent substances like tin or mercury, continue to have significant impact in the food chain due to their highly toxic effects and limited potential to chemically change to a lesser toxic form. Many allelochemicals which have significant bio-activity are far less persistent due the fact that they degrade quickly in normal environments to component parts which are not in themselves negatively biolimiting.

Copper is a nutrient for metabolism in most organisms but is toxic at elevated levels. The key differences are the concentration, duration of contact, and the organism(s)

involved. The chemical state of copper determines its ability to react, thus its ability to be assimilated, act as a catalyst in a biochemical or metabolic reaction, change the chemical bonding in a forming or curing polymer or composite, be a nutrient, be a repellent, or be a toxicant. Every organism handles copper a little differently with greater or lesser control of the fate of the copper as well as its own fate. Copper, as most transition metals, has varied complexing potential due to its ability to form bonds with ligands or molecular groups. In one embodiment, the copper is unoxidized. It is understood that the copper may be complexed with the excess polar groups of the media.

Copper exemplifies biolimiting agents and the variances of organisms to prefer, tolerate, or be toxified and/or killed by such biolimiting agents. Copper is everywhere in the environment. It is nearly always available somewhere in a habitat in sufficient supply, with location and bound form being the primary limits on its use. Generally available copper below 0.62 mg/l has no measurable negative effect in most habitats when considered generally available. In localized or sub habitat situations, however, it has been shown that from about 1 to about 70, or from about 5 about 60 or from about 10 to about 50 micro-grams ($\mu$g) $Cu^{2+}L^{-1}$ increases the heterotrophic activity of bacteria to the detriment of plankton which are intolerant and very copper sensitive. For instance, 20 milligrams (mg) of copper is toxic to Torla (=Candida) utilis, a yeast/fungi at pH 7 when in a simple form, however, when complexed the concentration for toxicity goes up proportionately. Also, 0.1 to 0.2 mg copper $L^{-1}$ is toxic to many species of molluscs. At 0.1 mg $L^{-1}$ of copper, the growth rate of *Ophyotrocha Labronica*, a marine invertebrate decreased significantly while at 1.0 mg $L^{-1}$ while *Artemia salina*, a very closely related species, found no change. (Corner & Sparrow 1956). Many such examples are found for copper as well as other agents. It has also been shown that many bacteria, which are at the interface of the uptake of nutrients as any entry way to the food chain, have the ability to store large amounts of copper which do not effect their general metabolism. This same storage capacity is demonstrated in zinc. In addition zinc ion activity has demonstrated a growth limiting effect at a very low concentrations for *Thalassiosira weissflogii*. In field tests of stenoprophiluric media in tropical waters, polymeric formulations of media had zinc as a replacement of copper with appropriate compositional shifts to relate to bioavailable zinc. These tests worked very well in open-ocean side by side comparisons to other media and agent combinations.

In one embodiment, the bio-limiting agent is copper. The copper is may be in the form of copper metal particles. These particles have an average size of about 20 $\mu$m to about 41 $\mu$m. In one embodiment, the particles have a cuboidal shape. In one embodiment, copper or copper alloy pieces are produced by chopping wire, e.g., circular or square-section, such that the particles formed have a length substantially equal to their diameter or maximum cross-sectional dimension. Similar shapes and forms yielding the same net bio-available effect may be accomplished by traditional atomization of molten copper in a controlled atmosphere where final shape is due to impingement or milling. Other sources of the copper particles may be electrolytic copper where the preparation of ingots or intermediate metal phases are not used. Alloys of copper, reclaimed or recycled copper, and impure copper may also be used. Thus, solid lumps of copper are produced rather than flakes or elongate filaments or the like.

In one embodiment, the copper particles have a shape such that the ratios of their major dimensions are all in the range of about 0.7 to 1.0. Thus, for example, if the particles are laid on a flat horizontal surface, they are all of approximately the same dimensions in plane and elevation and, for each particle, its two major dimensions in plane (i.e., a first dimension being the length of the particle in plane and a second dimension being the width in plane measured at right angles to the first dimension) and its elevation will all be in a ratio of about 0.7 to 1.0 with respect to each other. The particles are thus solid lumps and not flakes or elongate filaments. Each of the particles may be of polyhedral shape, or more specifically be in the form of a cube. Or, each of the particles may comprise a body having a rounded surface such as a cylinder or other shapes meeting this definition. Otherwise, the particles may comprise a mix of polyhedral bodies and bodies having rounded surfaces. The surface area and dissolution potential of the copper is adjusted in the final media or media by the particle shape and size and by the chemical state of the copper surface that is exposed in the media for ultimate contact with the micro-habitat.

The bio-limiting agent may be organic or inorganic compounds mixtures or blends, compounds or complexes or described as copolymers. Agents can be any component of the media or matrix which has bio-activity. Organotin copolymers in the media limit organisms by having tin as a component. Solvents, sols, mers, resins oligomers, catalysts, are included. Organic bio-limiting agents include pesticides, biocides, and herbicides. Combinations of bio-limiting agents may be used.

Nutrients

The media may be the source of nutrition for the organisms or may additionally contain one or more materials as additives which provide nutrition. Major nutrients needed for organism growth include elements or compounds such as C, H, N, Ca, and P. Minor nutrients are those elements or compounds required in smaller amounts, such as Fe, S, Al, Na, K, etc. Trace elements are those chemical elements required in minute amounts by a biological organism for health, growth, or survival. Trace elements include boron, cobalt, copper, fluorine, magnesium, manganese, zinc, iron, molybdenum, iodine, and selenium. Often the difference between two apparently identical micro-habitats which diverge radically in species and biomass are due to the absence of trace elements.

The bio-supportive matrix also contains at least one nutritional source. The nutritional source may be from the matrix polymer intrinsically, as an additive in the media matrix, or both. In some polymers peroxides are used as initiators or catalysts. In the final resulting media they may then become a nutrient. In an asphalt media, an oil used in the formation of the composite may become a hydrocarbon nutrient, a bitumen component may provide an alternate form of carbon. The nutrition source may be derived from any biologically available source in the media matrix.

The bio-mass requires, for example carbon, phosphorus and/or nitrogen to sustain life. It may also require minor nutrients such as silica and manganese, trace or even ultra-trace nutrients for a desired application as well. Silica may be used in composites such as asphalts as a source of silica. The sources of carbon include the polymers of the matrix, described below. Carbon may also be provided by the components of the other nutrients, such as a phosphate compounds or a complexed amine compound. The sources of phosphorus include natural or synthetic polymer components, catalysts and additives, such as phosphate compounds and/or salts containing $PO_4$. Examples of sources of nitrogen include amines, catalysts, additives and occluded compounds, such as salts of nitrogen and ammonia. The amines may be mono-or polyamines, including polyalkylene polyamines, such as diethylenetriamine, triethylenetetratamine, tetraethylenepentamine, etc. The nutritional additive(s) are present in amounts from ultra-trace levels to major source suppliers. Examples have been selenium and zinc. When the nutrients are supplied as additive to the matrix, then they are present, in one embodiment, at a level of 1 to 500 parts per million.

In one embodiment, the media may include one or more additives to provide nutrition such as amines, such as those described herein or fatty acids, such as those described herein. Fatty acids form the building blocks for lipids, oils, and waxes. Fatty acids involved in growth and health often are not synthesized by the organism(s). Therefore they must be included in the diet. They are required for cell membrane synthesis, and for fat metabolism. They make excellent media due to polymeric properties concurrent with nutritional properties.

In another embodiment, the media is formed with blow oils, dehydrated oils, varnishes, and natural resins, such as congo, copal, damar, kauri, phenolic, and coumarone-indene resins.

A plasticizer may be added to the media such as those formed from epoxy or phenolic resins, or composite or amalgamated media. The plasticizer or similar additive prevents vitrification of the material media.

Examples of plasticizers include phthalates, phosphates, citrates, adipates, tartrates, sebacates, succinates, glycolates, glycerolates, benzoates, myristates, and sulfonamides. Specific examples of these materials include dialkyl phthalate, dicycloalkyl phthalate, diaryl phthalate, dimethyl phthalate, dipropyl phthalate, di(2-ethylhexyl) phthalate, di-isopropyl phthalate, alkyl phosphate, aryl phosphate, tributyl phosphate, trioctyl phosphate, tricresyl phosphate and triphenyl phosphate; alkyl citrate, citrate esters, tributyl citrate, triethyl citrate and acetyl triethyl citrate; alkyl adipates such as dioctyl adipate, diethyl adipate and di-(2-methoxyethyl)-adipate; dialkyl tartrates, such as diethyl tartrate, and butyl tartrate; alkyl sebacates such as diethyl sebacate, dipropyl sebacate and dinonyl sebacate; alkyl succinates such as diethyl succinate and dimethyl succinate; alkylglycolates, alkyl glycerolates, glycol esters and glycerol esters such as glycerol diacetate, glycerol triacetate, glycerol monolactate diacetate, methyl phythayl ethyl glycolate, epoxidized soybean oil, octyl epoxy tallate, isooctyl epoxy tallate and so forth. Mixtures of plasticizers may be used.

For concrete applications, the above plasticizers may be used. Additionally, it is possible to use a hexametaphosphate, a tripolyphosphate, a polynaphthalene sulphonate, or a sulphonated polyamine as a plasticizing agent. In this embodiment, the plasticizer may also be a modified lignosulphonate or other material or a blend of lignosulfonate polymers or bentonite.

In one embodiment, amidoamines (polyamidoamines) with fatty acids are added to lower the viscosity of the media and provide alternative nutritional sources in the media. Fatty acids as lipids, oils, and waxes are essential nutrients and often cannot be synthesized by organisms usually found in a micro-habitat.

The media is generally prepared by mixing the media with the biolimiting agent. Since the media contains excess polar ingredients, it is useful to admix or premix the components to provide a consistent media. Typically, the media is divided into two parts, however the media may be divided into more parts such as three or even four for convenience. For purposes of illustration, the two part systems will be discussed. Because of excess functionality present in the media ingredients, pre-reacting the media ingredients provides a consistent and useful product.

For example, a media prepared with an excess cross-linking agent should be pre-reacted with a portion of the resin with the cross-linking agent. Typically the resin of the media is divided into parts. Part A is pre-reacted with the cross-linking agent. Part B is mixed with the bio-limiting agent. These two parts are then mixed and applied to a substrate. The application may be by any convenient methods for applying these systems, e.g., spraying, brushing, etc. Typically, one part of part A is used with from 1 to about 8, or from about 2 to about 6, or about 4 to about 5 parts of part B. The ingredients are mixed at room temperature for convenience. However, the ingredients may be heated as required for their successful reaction or handling. For instance, some media may need to be warmed to improve mixing (such as the tars and lacquers described herein). When pre-reacting a cross-linking agent, the cross-linking agent may be added portionwise to avoid an exothermic increase in temperature. It should be noted that the advantage of the present media systems is that the portions of the media may be packaged separately and then mixed at the application area.

The media is prepared by providing the material to be used in preparing the composite by adding at least one bio-limiting agent to the media. The biolimiting agent may be a part of the media substrate or may be present as a discrete material. In one embodiment, the bio-limiting agent is present in an amount of at least 2%, or at least about 5%, or at least about 10% by weight. The bio-limiting agent is present in an amount up to about 80%, or up to about 70%, or up to about 60% by weight. In some cases part per million concentrations of specific chemicals can account for limiting biological activity.

Peroxides may be added to the media as a source of additional reactive sites for biodegradation to occur or as an added nutrient for the attendant biomass.

A media may be prepared to use "polymer shrinkage" as typical in alkyd systems where polymerization binds the media to a substrate where the breakdown of the media is both chemical and physical following final cure, where the media shrinks and the rigid substrate does not, cracking and breaking of the media is caused. These cracks form more surface area of the media to be exposed and consequentially accelerate degradation.

In one embodiment, the media is formed from at least one maleated oil. The oils are described herein and include natural oils with or without unsaturation such as mineral oil, lard oil, pine oil, linseed oil, soybean oil, etc. The media is prepared using vinyl modified oils or styrenated, and vinyl modified alkyd resins are used to modify hydrophilicity.

In one embodiment, the media is prepared from a fatty acid or polyester resins which has grafted styrene, vinyl toluene, and or methyl methacrylate onto fatty acid resin chains. This same technique may be used in fatty acid oils rather than resins.

Polyethers prepared utilizing super acids ($F_3CSO_3H$), ($HSbF_6$), ($HPF_6$), or tertiary amines under acidic or basic conditions provide more flexible media.

In one embodiment, phenolic resins are added to polymers or composites or amalgams in order to reduce sites for hydrolysis in such resins systems as epoxies, blends, or mixtures.

The use of amine terminated polyethers such as polypropylene oxide as a di- or tri-amine branching system creates flexibility and additional sites for decomposition in the media.

Media may be prepared using cycloaliphatic amines such as diaminocyclohexane (DACH), isophoronediamine (IPDA) and 4,4' diamino dicyclohexyl methane (PACM). These amines reduce rates of degradation of the media.

Polyglycols may be used to prepare epoxy based media or similar media to improve flexibility or when accelerated biodegradation is desired.

Adjustment of the ratios or blends or stoichiometry of epoxy resin or blended systems of polyethyleneamines (DETA, TETA, TEPA) where phase separation causes a greasy exudate which can be used in itself as a cross-link modifier, biolimiting agent, or nutritional source.

Formation of a media using high solids, 500 to 3,000 EEW, where a glycol is used to alter the polymer to permit a biodegradation rate in sea water at 1–2 mils/year (thousandths of an inch) in tropical climates can be used. In Fajardo, Puerto Rico this amount is 8.5%±1.0%.

Control of the molecular weight of the polyol component and oxazolodines in an isocyanate media are used to control cross-link or polymerization sites. Also a copolymer can act as a moisture scavenger to manage hydrophilicity of the resulting media, usually requiring pre-polymer or adduct formations.

Other combinations which could be formulated to meet specific criteria of a targeted habitat include the use of many other agents or mixtures of agents in these water based systems. While designing specialty agents, nutritional sources which are biolimiting in themselves to the biomass may be employed. Many forms of algae and other marine forms, as an example, are limited in their growth and numbers in a habitat by the absence of iron. When iron is added to the habitat an explosive growth of the starved organisms occurs. This can be another dynamic of a stenoprophiluric system, where the addition of a nutrition-limiting agent also assists in the design of the consortium of organisms in the biomass of the micro-habitat.

Providing for these unique media cross-link agents which are helpful in managing the dispersion include acrylic melamine, intermediates of functional groups containing allyls and similar agents to facilitate the final media formation where the dispersal and homogeneity of the matrix, is required to manage the dose requirements or levels of bio-availability of the agents and nutrients.

In one embodiment, fatty acids are added to any polymer, composite, or amalgam to increase oxidizable properties. The fatty acids include unsaturated fatty acids such as oleic, linoleic, and linolenic acids. Conjugated double bonded fatty acids may also be used such as -eleostearic acid, The fatty acids may be naturally occurring or synthetically derived. Other fatty acids include ricinoleic and stearic acids.

In one embodiment, mercaptans and/or polysulfides are added to the media to increase flexibility.

It should be understood that in addition to the components described above, the stenoprophiluric media may also contain pigments. A variety of pigments may be utilized. Inorganic pigments which are useful include metal powders such as aluminum or bronze, titanium dioxide, silica, iron oxide red, talc, mica, clay, zinc oxide, aluminum oxide, magnesium oxide, strontium chromate, zinc chromate, cadmium sulfide, carbon black, lead chromate, zinc chromate, molybdate orange, calcium carbonate and barium sulfate. Organic pigments also can be used and these include Para Red, Lithol Rubine, Halio Bordeaux, Thio Indigo, Thio Indigoid, Toluidine, Dioxazine, Red Lake C, Red Lake R, Anthraquinone, Xylidide, Phthalocyanine Blue, Phthalocyanine Green, Azo, etc.

In one embodiment, the media is prepared with at least one drying agent. The drying agents include organometallic complexes of cobalt or manganese. The organic complex may be for example a metal octoate or napthenate salt. Other metals which can be used in the drying agent include salts of lead, zirconium and calcium.

In one embodiment, the media includes unsaturated polyester resin, with a greater control over oxidation sites in the matrix achieved with the addition of an insoluble wax, such as natural wax, polyethylene wax, etc. The wax may be in one embodiment, semi-crystalline wax. The wax may be used with any of the above polymers such as the polyester resins.

Oxygen scavengers may be included in the media. Examples of oxygen scavengers include allyl ethers and various amines. Curing of the polymers may be accomplished with high intensity lamps for UV cure to control oxygen levels in the final media. Alternatively, to control oxygen in the matrix media, the formation of the media can be completed in an inert atmosphere.

In one embodiment, the media also contains surfactants, soaps, clays, or other dispersion modifiers to help with the dispersion of the ingredients. Examples include but are not limited to; tertiary amines, metal salts, chelates, organometallic compounds, oxazolodines, primary amines, secondary amines, peroxides, acids, bases, etc. Clay dispersive agents, such as bentone, may also be used.

Use of agents in a media, as detailed in other parts of this disclosure, include various methods of providing the agent throughout the media at an availability and concentration for a desired effect. This dispersal can be accomplished by inclusion, occlusion, attachment as a functional component of a molecule or mer, changing the size of the particulate containing the agent which could be an inert or non-reactive secondary carrier of the agent. The agent could be incorporated onto a coating of a particulate such as a sand or grit, proppants as used in the oil and gas industry, ceramic spheres, glass beads, clay particles, or micro-capsules. The release rate or bio-available rate and concentration could be altered as desirable by adjusting the coating parameters similarly as is done with a media in the context of this document.

An agent could be encased or coated or isolated such that, until such time as the matrix is removed, the agent is totally inactive. The agent could be an organism or micro-organism as a bacteria, which could be freeze dried and stored in the matrix of the media which until exposure through the loss or degradation of the media and the re-hydration from the host habitat, micro-habitat, or general environment, the organism is activated. Similarly an agent could be a nutrient stored for delayed release. An agent could be a seed or spore which in concert with other components of the media could provide a delayed introduction of an agent and/or nutrient and/or new organism to the host or micro-habitat, ultimately reaching the general habitat, then the environment for remedial or restorative purposes.

Another method of dispersing an agent in a media would be to form polymers with agents which are completely cured. After curing, the media is segmented by cutting or grinding or both to a desired particle size, typically 10 to 100 microns in size, and placed in composites or amalgams. One such example would be a copper/epoxy media with desirable properties which is incorporated into an asphalt or silicone jelly amalgam.

In one sense the use of a media which is sacrificial or degrades over time becomes a new form of release mechanism. In toxic coatings, soluble media or insoluble media delivery systems effect a release of an agent or toxic substance. The release mechanism, which is stenoprophilurea, exhibits a novel equilibrium between the micro-habitat and the host habitat. This equilibrium results from the management of the biomass on the media by the agent or toxin. By affecting the biomass, the release mechanism either speeds up or slows down the degradation of the media which exhibits a novel equilibrium between the micro-habitat and the host habitat. Along with this, meaning in addition to or concurrently, an agent could be used to provide another effect at a delayed time. The agent or a separately contained or occluded component could be for a different purpose. Particularly where time or place of delivery of an agent is not accomplished either readily or economically via other means, the mechanism could be used to provide a timed release of chemical agent, biological agent, or organism of significance. In a habitat restoration process, missing nutrients or organisms could be released at designed times at a dose required to limit or manage impact. In a closed system very extreme chemicals could be used for managing scale, increasing or reducing friction, or many other purposes. In a down hole application for drilling of oil and gas, treatment chemicals could have a delayed delivery using this mechanism. In some cases seed dispersal, microbe introduction or other biological effect could be employed.

Micro Habitat Formation

The stenoprophiluric media interacts with the host habitat to form a biomass on the surface of the media. The biomass is a colonized set of an organism(s) or a sub-set (or consortium) of organisms of the host habitat. In one embodiment, a desired organism may be added to the habitat. Microbes, such as bacteria and other simpler forms of primary producers, on the surface of the media, move substances into the food chain. The surface is the richest source location for nutrients. Participation in the consortium or colony is also controlled by the concentration and availability of any and all biolimiting agents. The biomass formation on the biological side of the interface often forms a layer, which has been referred to colloquially as "slime city". This layer of biomass on the surface of the media precludes participation of additional organisms. The layer may form polysaccharide masses which provide support for the biomass as well as nutrient sugar storage. The slime often contains pathways for the introduction of water and the transport of waste out of the layer. On the media side of the interface the bioavailability of nutrients and agents directly effects the concentration, numbers and kinds of organisms participating in the layer or adjunct biomass. In this invention, the biomass actually participates in the decomposition of the media as a food source. Only those organism (s) which require, find tolerance, or have the ability to survive the combination of nutrients and agents sustain themselves at this location. Then the biomass, in its increased demand for nutrients, decomposes the media which exposes the next layer of nutrients and agents in the media, either by consumption, enzymatic dissolution, and/or chemical dissolution, with support or synergies from the host habitat. The media then is sacrificial by design to the biomass. The importance of formulation of the media and level of agent activity can be modified to either speed up or slow down the success rate of the biomass in degrading the media. This relationship of medial biolimiting agent and biomass is stenoprophilicity.

In the context of a habitat, being down stream from a wastewater treatment plant which constantly emits an effluent rich in nutrients and other biolimiting agents will shift the numbers and kinds of organisms which inhabit the space at this location. Then as long as the nutrient load and agents persist or dilute down gradient, the numbers and kinds of organisms may become more like the biodiverse community ahead of the injection point. Prior to the injection point usually the habitat has many kinds of organisms, each represented by a few numbers of each species. After the injection point, a sub-habitat or micro-habitat is formed which typically due to the change in conditions will have the effect of greatly reducing the number of species represented in this micro-habitat, but the number of individuals in those species may be in the millions. In this example, sludge worms predominate the biomass, represented by millions of those individuals per square meter, where upstream in the diverse habitat only one individual per 3 square meters of river bottom is typical. Other examples are seen in nature. In the ocean, at the location of a sulfur vent on the ocean floor, a very limited number of species find this location attractive and they are neither aerobic or anaerobically based organisms. They are facultative and tolerant of the resources at hand. Many organisms like bacteria adapt over time, often to tolerate a new condition.

The present invention creates a media with nutritional and biolimiting properties which form a stenoprophiluric media. The composition of the media determines the likely organisms to create the micro-habitat. Therefore, the media, the agent and the biomass form an interactive intermediate zone which adopts characteristics different from the host habitat and the substrate. This zone is a gradient of biological and chemical and physical parameters which define the interface. The media plus a layer of microbes, such as bacteria or algae, may be another representation of the invention. In a hydrophytic environment, the invention may be a media with a mold or yeast as the biologically active component. The micro-habitat could be a colony of single species like protocists in a marine slime net called Labyrinthulata. The micro-habitat could be bacterial community as found in freshwater Northern Pike fish slime. The micro-habitat could include a consortium of species like that in the stomach of a cow where five different species of bacteria form a very complex symbiotic set of relationships. The micro-habitat could be a group of bacteria and mold spores found on sap or detritus.

The present invention is the selection of media, biolimiting agents, and organisms in a combination that provides for the sacrificial consumption of the media over an extended period of time. The media and the biomass isolate the substrate from degrading effects from the environment or organism of the habitat. It is important to note that the organisms associated with the assimilation of specific agents become less attractive to many other species who would normally use the organism as a food source. Thus, limiting the desirability of an organism as a food source limits the settling of higher life forms and precludes attachment replacement of the lower organisms from predation of higher organisms. The additional benefit of the invention is that a healthy biomass has the ability to defend its ecological niche via the use of allelopathy. Allelopathy is where metabolites of the biomass, typically classified as secondary metabolites, are present as extra-cellular compounds which have a new bioactivity above and beyond the effect of the biolimiting agent in the media. In fact, allelochemicals may be used in the preparation of a stenoprophiluric media as an agent. However, the invention is not predicated on the use of or the secondary production of allelochemicals. Allelopathy is simply an added benefit used by the biomass for self preservation or protection.

By adjusting the physical and chemical properties of a stenoprophiluric media, the resultant media provides for the natural creation of a micro-habitat which possesses the ability to defend and protect its position in the production of allelochemicals. An epoxy media can be produced to degrade in marine habitats at a rate of 1 mil (thousandths of an inch) per year with adjustments to the cross-link density by excess stoichiometry of the curing agent, such as an amine, with additional compositional parameters, such as occluded copper particles, which effect the potential for degradation by naturally occurring organisms in seawater. While adjustment of any of the physical and chemical properties of the formation may work, the addition of a glycol of 8% in the admix with a stoichiometric excess of 0.5 of the amine and a 55% by weight loading of a particulate copper produces a stenoprophiluric media which lasts for many years. By adjusting the final cure or formation, the media, where opportunity for degradation is enhanced by the addition of more degradation sites with the glycol and the excess amine, create a more degradable media than is found in the practice of normal epoxy systems. By increasing the number of sites in a polymer where hydrolysis, dissolution, oxidation, or degradation can occur, the rate at which dissolution and ultimate total decomposition of the stenoprophiluric media over time occurs is affected. Enhanced biodegradation potential results in a media that is more interactive with a host habitat and essentially becomes an interface.

The bio-supportive media is biologically active. In other words, the media is affected by the biomass. In fact the bio-supportive media may be at least partially consumed by the bio-mass. In one embodiment, a polymer of urethane and zinc metal is consumed at a rate between 0.5 and 10 mils (thousandths of an inch) per year. The biomass provides isolation of the substrate, in this case a slow RPM propeller, from corrosion from seawater while the propeller is in stand-by mode.

Substrates

The stenoprophiluric media is placed onto a substrate. The substrate is prone to degradation from the environment of its habitat. The substrate may be a any material in need of the protection provided by the stenoprophiluric media. Example of substrates includes metal, wood, cement, concrete, etc. Typically, the stenoprophiluric media is placed onto a metal (e.g., steel or iron), fiberglass, cement or concrete substrate. If the stenoprophiluric media is being prepared as a pedigree panel then it may be placed onto glass, polycarbonate, etc. The media typically has a thickness of from about 5 to about 100, or from about 10 to about 80, or from about 20 to about 60 mils.

The substrate may be a vessel hull like that of a boat or ship. The boat hulls may be made of wood, fiberglass, aluminum or steel, or the hulls may have a rubberized coating. The bio-supportive media may also be applied to other marine structures, such as pilings, floats, and buoys made of the above listed materials or concrete. The substrate may also be any surface which supports the bio-supportive media and which provides the needed structural support for the media and biomass. The substrate could be a culvert or piping that provides a support for the bio-supportive media and biomass. A resultant biological barrier (biomass, biofilm) may be established using the bio-supportive media, biomass and substrate. The substrate may also be a structural support or surface expanding area as in a vessel such as a fermentation vessel. The substrate could be any existing structure in an aqueous or hydrophytic environment. The substrate could be a sheet, film, or cast form. Allelochemicals may be separated from the biomass as they are produced.

In one embodiment, the media and subsequent bio-mass forming the micro-habitat must be isolated from any substrate, such as steel or metal where the host habitat can corrode, oxidize, hydrolyze, or in any way make available to the consort of organisms a decompositional product of that substrate. In effect, Fe, Mn, Cr, Cd or any other metal, compound, or chemical from that source could change or alter the micro-habitat. The dissolution product may become a nutrient or bio-limiting agent which may be undesired and significantly change the micro-habitat. Consequently, base and mid coats are employed. It may be advantageous to place one or more intermediate coatings, or mid-coats, between the stenoprophiluric media and the substrate. These layers are typically commercially available coatings which provide insulation of the media and substrate. The mid-coats may also be used as a primer to improve the adhesion of the stenoprophiluric media to the substrate. The mid-coats may be filled or unfilled. The fillers are known to those in the coating arts, such as chopped glass, fiberglass, titanium dioxide. The mid-coats typically have a thickness from about 2 to about 20, or 4 to about 16, or from about 6 to about 14, or from about 8 to about 12 mils.

Marine Applications

A typical example for a ship or hull is where a media, such as a polymer coating, comprising a two part system, e.g., an epoxy-glycol-amine polymer, is formed on a substrate and is bio-degraded at a rate of about 0.5 to about 2, or from about 1 to about 1.5 mil per year. The media is occluded with metallic copper particles (a bio-limiting agent) with access to biologically available copper having a cuboidal shape with a surface area of 0.18 $m^2/g$, a bulk density or 3.2 g/ml and an average particle size of 29 microns, which provides a media for the support of a unique biomass composed primarily of bacteria and algae, and which creates a unique micro-habitat. The organisms comprising this biomass, in turn, have the ability to generate allelochemicals and thereby exhibit allelopathic properties. The media comprises a biolimiting agent (copper) and a nutritional agent (components of the polymer).

In the specification and appended claims the term allelochemicals refers to the metabolic reaction products of a biomass. Typically the allelochemicals are secondary metabolite reaction product(s) of a biomass.

In one embodiment, copper is a useful agent of choice due to its useful biolimiting ranges. Copper is an essential nutrient at very low levels, i.e., 1–2 parts per million. It is also well understood as a biolimiting agent at many other concentrations. Lethal doses for some species occur at 10 ppm, in other classes of organisms biolimiting does not occur until 40 ppm.

Specific organisms can be targeted for specialized purposes. Slick "no drag" hulls have been sought for centuries. The slickest surface is not a waxed or polished or Teflon surface, contrary to common belief. Using biomimicry, most fish have a clearly articulated slime layer of complex proteins, polysaccharides and bacteria. They are very fast and achieve this speed from the physical/chemical interface of water molecules with the surfaces of the bacteria and components which harbor either thinly affixed water molecules or compounds which have the appropriate hydrophilicity/hydrophobicity balance. This embodiment can be achieved with a higher concentration of copper usually at 65% with the addition of an additional biodegradation rate accelerator in the form of a catalyst or chain stopper which shortens the length of the chains in the polymer being used. Often this targeted species has known tolerances and/or preferences for the specific bio-limiting agent. In the above mentioned example using copper, certain Algae and bacteria prefer an environment or micro-habitat with copper constantly available from 5 to 15 $\mu g/cm^2/day$. The bio-limiting agent may provide nutrition for one organism while concurrently being a toxin or repellent for another organism of similar or dissimilar species. Most algae and bacteria can not tolerate this level. Barnacles and zebra mussels can not tolerate any copper.

Stenoprophiluric Substrate as Natural Barrier for Migration

Schistosomiasis is the leading cause of blindness and morbidity in many third world countries. A parasite which causes this infectious disease is hosted by snails. The present embodiment is the production of a coating either polyurethane, polyepoxide, or polyester or a blend of these where the agent is occluded copper metal. The copper is present at 62% by weight of cuboidal or more spherical shapes which present significant surface area to produce a bio-available amount of copper at 3 to 4 micro-grams per square centimeter per day. This media is affixed or coated onto irrigation pipes or at all points of entry of irrigation waters with appropriate baffles to insure water contact with the media. Effectively, this copper concentration will form a barrier for the snails and prevent infestation of the irrigated fields or rice paddies. This is normally sufficient to prevent migration and may be adjusted either up or down by changing the percentage of copper in the media which in turn reduces or increases the concentration of available copper as needed due to climatological or local environmental conditions. A coating of 50 mils could last for up to 35 years and be effective for that entire time due to the sustained very low concentration of available copper at the surface which is not discharged, thereby ensuring that no host habitat degradation occurs.

The primary function of the copper in this example is for repulsion of copper-abhorring snails. Concurrently the biomass, primarily comprised of photosynthetic algae and copper loving bacteria further are expected to provide these allelochemicals which reduces the amount of copper needed to be successful in biolimiting the travels of the snail. It must also be noted that alleochemicals by design quickly degrade themselves and do not become long term bioactivants, unlike most man-made agents which have been used, such as commercial pesticides or high concentration of copper sulfate, the use of which are banned in these countries. The bio-limiting agent acts to alter the ability of undesired organisms to compete for resources in the local or surficial surface environment, the micro-habitat.

Stenoprophilicity instead of Biocides in Water Systems

Many water systems become active fouling and corrosion zones due to the heat transfer or substrate warming locations. Under oxygenated aqueous conditions, which normally concentrate nutrients over time due to evaporation of nutrient filled waters, fouling and corrosion can become very active. One embodiment of the present invention is the formation of a coating, such as a polyester or epoxide or urethane media, where cross-link modifiers are included which shorten the molecular structures of the resultant polymer. This media with the inclusion of very low amounts of molybdenum or vanadium measured to be actively limiting where the bioavailability in the media is in the parts per million range is very effective for long periods of time. Instead of maintaining the biolimiting concentration in the water stream, the only place where the biolimiting agent is located is in the surface-protecting media which protects the substrate. This in effect eliminates direct discharge of quantities of "biocides" in the circulating water when "blow down" occurs, due to ineffective biocide concentrations or excessive build up of scale and suspended or dissolved solids in the water, which attenuates corrosion.

Multiple Agents

The bio-limiting agents include organic or inorganic bio-limiting agents or combinations of agents. Oil production and/or drilling platforms have serious problems with fouling. As much as 40% of structural costs for marine platforms are to compensate for weight build up in the fouling zone. The fouling zone is the top 30 meters of the platform which may be as tall as 300 meters. Stenoprophiluric media containing either copper, zinc or organic agents, such as Sea Nine 211, singly or in combination can be used as a top coat to film, sheet, or tape which is affixed to an existing platform with interstitial cementitious material to battle corrosion. These appliques often solve or delay corrosion problems with a useful biomass comprised of algae, diatoms, and bacteria which can limit to a simple slime layer the biomass which is in residence. The biomass has the additional benefit of eliminating grass formation which causes much drag as well an interferes with routine maintenance and inspection procedures.

Alternate Sources of Nutrients

The media composition includes a support for the media, such as a polymer, a composite, a cohesive mixture of naturally occurring substances such as tar or resins, or other supporting media, such as concrete. The polymers may be natural or synthetic polymers. The media could also be cementitious aggregates as well. The media could also be constructed like many natural ceramics, where limestone is the media and starch is the binder. The polymers can be bio-polymers or bio-engineered polymers. The polymer may be any polymer which can sustain the bio-supportive media. The polymer, by sustaining the bio-supportive media, provides the physical characteristics or environment needed to maintain the bio-limiting agent and other additives of the media as well as the biomass.

Changing the Biodegradation Rate and Bioavailability of the Agents

The stenoprophiluric media is consumed at a preferred rate by the biomass but still has sufficient hardness to provide durability to prevent destruction of the media. By altering the cross-link density and/or the porosity and/or solubility, the bio-availability of the media material, nutrients and bio-limiting agents thereby form the bio-supportive media. Alteration of the cure of polymers resulting in changes of the cross-link density, interrupting the gel length, modifying the amount of sol incorporated or washed out, chain stopping, functional group manipulation, copolymerizing, introduction of occlusions, solvents, or water, changing the heat of reaction, providing admixes, pre-mixes or step-wise polymerization to achieve new compositional structure, to provide for the management of the deterioration and solubility, and/or the hydrolyzation and/or the oxidation of the media where a desired biodegradation rate is achieved can be used.

Adjusting the stoichiometric ratios of the basic polymer system may also be used. In the previous example of an amine, glycol, epoxy system, the amine was varied to be in excess of stoichiometry by 1.5, 2.0, and 3.0, holding the copper particulate constant. The resultant media showed differences in abiotic elution of copper into seawater and, by changing the amount of biomass comprising the slime micro-habitat, showed changes in both the numbers and kinds of organisms present.

In a similar test where the amine and polymer media were held constant and the copper concentration (of a uniform particle) as a percentage of composition was varied from 25% to 70%, the bio-mass of the micro-habitat slime decreased in volume as the percentage of copper increased. By including or excluding additional components to the media, desired properties can be achieved for various requirements.

Mechanical and Stenoprophiluric Properties can be Compatible

The durability of the bio-supportive media is related to its application. For instance, when used as a fouling coating, the bio-supportive media provides sufficient strength to prevent abrasion and therefore removal of the media from the surface to be protected from fouling organisms. In structural applications the media may be more resilient to provide 10 to 20 year service life with modified consumption rates where abrasion is less of a concern.

The polymers used may be any of those which are compatible with the bio-limiting agent and/or nutritional source. It should be noted that in one embodiment, the polymer is a nutritional source for the biomass. These polymers include any natural or synthetic polymer including those used in fouling paints and coatings. The polymers may be polyepoxides, polyurethanes, polyesters, rubbers, latex, styrene, elastomers, acrylics, acetoacetates, acetoacetamides, and bio-engineered polymers as well. In another embodiment, the media includes polymers or copolymers of acrylonitrile, methacrylonitrile, acrylamide, methacrylamide, vinyl chloride, vinyl acetate, acrylates or methacrylates, styrene, vinyl-isobutyl ether, benzaldimine, aldimine, araldimine, acetoacetoxyethymethacrylate, adimine, t-butylaminoethyl methacrylate, carboxyl groups, vinyltoluene-acrylate copolymers, epoxy- or coal tar epoxy-systems, etc. Other hydrophilic or partially hydrophilic polymers derived from modified blends such as other epoxies, urethanes (nitrogen source), rubbers, elastomers (carbon source), and bio-polymers (natural and synthetic, including bio-engineered) may also be used. Any blend or combination of components which facilitates the appropriate polymer degradation rate within a prescribed bio-agent dissolution or elution rate can work.

Additional Embodiments

In one embodiment, the media contains a natural or synthetic rubber. Examples of these rubbers include polysulfonated polyethylenes, of which Hypalon is one example, ethylene propylene diene monomers, styrene butadiene rubbers, bromobutyl rubber, chlorinated rubbers, such as chlorobutyl rubber, polychloroprenes such as Neoprene and nitrile rubbers.

In one embodiment, a catalyst or cross-linking agent such as the polyamines described herein (e.g., triethylene tetraamine) serves as a cross-link modifier and a nutrient. The excess amine interferes with the polymerization, increasing the porosity, lessening the cross-link density, and consequently the surface area where biodegradation can occur at a favorable rate, which in turn permits the dissolution of occluded copper at approximately 10 to 20 micrograms of copper per day. Similar results may be obtained by substituting a portion of the amine with other functional amine groups or catalysts employed as either physical property modifiers or cross-link density adjustments.

In one embodiment the polymer contains functional acetoacetate groups polymerized with functional amines to form enamine complexes with bio-limiting agents. Single bio-active agents in part per million concentrations or as co-active agents in concert with any traditional anti-fouling agent(s) could likewise be used. In certain applications, blends with other traditional polymers and catalytic components and/or modifiers inert or active could provide additional beneficial properties.

In one embodiment, an epoxy media polymer with elution rates of copper between 30 and 50 micrograms per square centimeter per day is employed where genetically altered organisms are supported for studying new drug and fine chemical applications of allelochemicals occurring in such small and fragile concentrations that in-situ natural environmental habitats are required.

In one embodiment, a urethane polymer with vanadium compounds as an active bio-limiting agent is utilized to eliminate the use of biocides in closed loop cooling water systems thereby averting the need to discharge biocides into the environment.

In one embodiment, a coal tar polymer and copper metal are utilized on a concrete vault in a hydrophytic (a wet or submerged environment in, e.g., a tropical climate) environment protecting communication equipment and consumption of the concrete by native organisms.

In one embodiment, affixing a modified epoxy and copper metal media to is a sheet or film is applied to the water line of a boat or vessel to impede settling of zebra mussels in fresh water habitats.

In one embodiment, an elastomer media with copper metal particles and a dispersal of isothiazolone in the media provides an excellent media for the protection and maintenance of wood members used in marina construction extending the useful life of the wood pilings and docks to 25 years. The isothiazolone enhances the biofouling control properties while the metal particles protect against marine boring organisms.

In another embodiment, the media contains an epoxy resin. The epoxy resin is prepared by reacting an epoxy containing prepolymer and a crosslinking agent. Typically the epoxy resin is prepared from Epichlorohydrin bis-phenol A and a suitable cross-linking agent, such as an polyamine, such as those described herein. The amine is used in excess of the amount needed to react with the epoxy pre-polymer. The ratio of the amine to the epoxy pre-polymer is typically from about 0.75–4:1 or about 0.9–2:1, or about 1–1.5:1.

As described herein the bio-supportive media contains nutritional additives and bio-limiting agents. The media may be formed from any polymer, composite, and or amalgam where the biodegradation rate may be adjusted to facilitate an agent which produces a micro-habitat distinct from the substrate and the host habitat environment. The media typically has a thickness from 2 or 3 mils (thousandths of an inch) but is equally serviceable as a media having a thickness of 40 or 50 mils. In certain applications a shape or form could be used to have a much greater depth as well. The media is consumed by the biomass over extended periods of time while at equilibrium with the external environment and the bio-limited biomass as allelochemicals are produced. Design of a system to endure the length of time required to live out a useful service life could take on very large proportions.

Pharmaceutical Applications

As a tool for encouraging natural production of candidate compounds for pharmaceutical or fine chemical use, supportive media are produced with competing organisms. Once these micro-habitats are established on prepared and equilibrated, distinctly different media forms, they are brought into juxtaposition to create a physical space competition thereby triggering the natural allelopathic reactions with associated allelopathic compounds, pre-cursors, and by-products.

In a further step, a media is produced where the nutrient and bio-limiting components are selected to foster a specific organism(s) which are absent from the intended environment. The media is then introduced and inoculated or the absent organism is introduced which now facilitates the formation of a micro-habitat where attributes such as re-introduction of species due to environmental upset such as pollution or spill is facilitated. In the case of closed or partially closed systems, a natural system of biomass succession control can be achieved limiting the biomass formation and preventing fouling of unwanted biomass development in cooling water systems, fire suppression systems, and similar locations where biological growth diminishes the systems' functional capacity. Cooling water watercourses and water uptake systems for utilities are such examples.

The following examples are non-limiting and provide illustrations of the stenoprophiluric media of the present invention. These materials may be applied to one of more of the substrates described herein to provide protection from fouling, for example. Unless otherwise indicated, the amounts are by weight, the temperature is ambient temperature and pressure is atmospheric.

EXAMPLE 1

A stenoprophiluric media is prepared by separating an amount of epoxy resin available commercially as Araldite 508 into two portions. The first portion (Part A) comprises a quarter of the total resin. To Part A is added a 1.5 stoichiometric excess of triethylenetetraamine (TETA) portionwise to avoid excessive exothermic temperature increase. To the other portion of the resin is added copper powder having a cuboidal shape and having a surface area of 0.18 $m^2/g$, a bulk density of 3.2 g/ml and an average particle size of 29 microns, and Araldite 6004 (poly-glycidal blend for flexibility and hydrophilicity). The copper is added at an amount to have 55% copper in the resulting mixture. The amount of Araldite 6004 is 0.43 parts for each part of Araldite 508 in Part B.

The admix ratio of the media is 1 part of Part A to 4 parts of Part B. Parts A and B are combined and then are applied to a substrate such as a boat hull.

The above bio-supportive media is employed by adding the media to a boat hull with appropriate base adhesion coat and mid-coat for corrosion and insulation barriers to bimetallic galvanic actions, to prevent adherence of barnacles and other undesirable organisms.

EXAMPLE 2

A stenoprophiluric media is prepared by mixing 4 parts of a mixture prepared from a mixture of 292 parts of Araldite GY 508 and 199 parts of TETA, and one part of a mixture of 870 parts of Araldite 508, 499 parts of Araldite 6004 and 1993 parts of the copper powder of Example 1.

EXAMPLE 3

A Stenoprophiluric media is prepared as described in Example 2, except that trishydroxy amino methane (THAM) is used in place of the TETA. The THAM replaces TETA on an equivalent basis.

EXAMPLE 4

A Stenoprophiluric media is prepared as described in Example 2, except that Araldite 6004 is not used and 50 parts of neopentylglycol is added to Part B.

EXAMPLE 5

A Stenoprophiluric media is prepared as described in Example 2, except that glycerine is used in place of the TETA. The glycerine replaces TETA on an equivalent basis.

EXAMPLE 6

A Stenoprophiluric media is prepared as described in Example 2, except that additional 50 parts of Jeffamine D-230 is added to Part A.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A bio-supportive medium comprising:
   a degradable material;
   at least one nutritional source; and
   at least one bio-limiting agent dispersed in the degradable material;
   wherein the degradable material, the at least one nutritional source, and the at least one bio-limiting agent are provided in quantities, such that the bio-supportive medium is capable of supporting formation of a biomass having at least a specific consortium of organisms of identical or different species, substantially at equilibrium within its environment or host habitat; wherein the at least one nutritional source and the at least one bio-limiting agent are selected to control the amount and type of species present in the biomass.

2. The medium of claim 1 wherein the bio-limiting agent is a metal or organic toxin.

3. The medium of claim 1 wherein the bio-limiting agent includes a tin, copper, or nickel metal, alloy or organic complex.

4. The medium of claim 1 wherein the bio-limiting agent is a copper or copper alloy particle.

5. The medium of claim 1, wherein the degradable material is formed from a polymer, composite, or amalgam.

6. The medium of claim 5, wherein the degradable material is a polymer, and the polymer is a thermoplastic or thermosetting polymer.

7. The medium of claim 5, wherein the degradable material is selected from the group consisting of: an epoxy, a polyester, an aminoplast resin, a phenolic resin, an acrylic resin, a silicone resin, a silicone jelly, a lacquer, and a polyurethane.

8. The medium of claim 5, wherein the degradable material is an amalgam of naturally occurring tars and resins.

9. The medium of claim 5, wherein the degradable material is a composite.

10. An article comprising a bio-supportive medium according to claim 1 adhered to a substrate.

11. The article of claim 10 wherein the substrate is a metal, wood, concrete, or fiberglass.

12. The article of claim 10 wherein the medium is adhered to the substrate by one or more intermediate polymer layers.

13. The article of claim 10 wherein the substrate is a vessel hull.

14. The medium of claim 1, wherein the degradable material comprises at least one epoxy resin.

15. The medium of claim 1, wherein the biolimiting agent is a substance, compound, element, or molecular complex which has a specified bioactive property.

16. The medium of claim 1, wherein the bio-limiting agent is a heavy metal, an organo-metallic, an organic biocide, a phenol compound, a thiadiazole compound, or a thiocarbamate compound.

17. The medium of claim 1, wherein the nutritional source is present in the degradable material or an additive to the degradable material.

18. The medium of claim 1, wherein the degradable material is biodegradable and is consumed by at least some species in the biomass.

19. The medium of claim 1, wherein the degradable material serves as a nutritional source to at least some species in the biomass.

20. A bio-supportive medium comprising:
a degradable material selected from the group consisting of: an epoxy resin, a polyester resin, a polyurethane resin, and an aminoplast resin;
at least one nutritional source; and
at least one bio-limiting agent dispersed in the degradable material;
wherein the degradable material, the at least one nutritional source, and the at least one bio-limiting agent are provided in quantities, such that the bio-supportive medium is capable of supporting formation of a biomass having at least a specific consortium of organisms of identical or different species, substantially at equilibrium within its environment or host habitat; wherein the at least one nutritional source and the at least one bio-limiting agent are selected to control the amount and type of species present in the biomass.

21. The medium of claim 20 wherein the bio-limiting agent is a tin, copper, or nickel metal, alloy or organic complex thereof.

22. The medium of claim 20, wherein the degradable material is an epoxy resin or a polyurethane resin.

23. The medium of claim 20, wherein the degradable material comprises at least one epoxy resin.

24. The medium of claim 20, wherein the bio-limiting agent is a substance, compound, element, or molecular complex, which has a specified bioactive property.

25. The medium of claim 20, wherein the bio-limiting agent is a heavy metal, an organo-metallic, an organic biocide, a phenol compound, a thiadiazole compound, or a thiocarbamate compound.

26. The medium of claim 20, wherein the nutritional source is present in the degradable material or an additive to the degradable material.

27. A bio-supportive medium comprising:
a degradable material of a crosslinked polyepoxide prepared from an epoxy resin and a polyamine crosslinking agent;
at least one nutritional source; and
at least one bio-limiting agent dispersed in the degradable material;
wherein the degradable material, the at least one nutritional source, and the at least one bio-limiting agent are provided in quantities, such that the bio-supportive medium is capable of supporting formation of a biomass having at least a specific consortium of organisms of identical or different species, substantially at equilibrium within its environment or host habitat; wherein the at least one nutritional source and the at least one bio-limiting agent are selected to control the amount and type of species present in the biomass.

28. The medium of claim 27, wherein the biolimiting agent is a substance, compound, element, or molecular complex which has a specified bioactive property.

29. The medium of claim 27, wherein the bio-limiting agent is a heavy metal, an organo-metallic, an organic biocide, a phenol compound, a thiadiazole compound, or a thiocarbamate compound.

30. The medium of claim 27, wherein the nutritional source is present in the degradable material or an additive to the degradable material.

31. An article comprising: a substrate, which is prone to degradation and corrosion; a bio-supportive medium in contact with the substrate; and a biofilm sustained on the bio-supportive medium;
the bio-supportive medium comprising:
a degradable material;
at least one nutritional source; and
at least one bio-limiting agent dispersed in the degradable material;
wherein the degradable material, the at least one nutritional source, and the at least one bio-limiting agent are provided in quantities, such that the bio-supportive medium is capable of supporting formation of a biomass having at least a specific consortium of organisms of identical or different species, substantially at equilibrium within its environment or host habitat; wherein the at least one nutritional source and the at least one bio-limiting agent are selected to control the amount and type of species present in the biomass.

32. The article of claim 31, wherein the degradable material comprises at least one epoxy resin.

33. The article of claim 31 wherein the substrate is a metal, wood, concrete, or fiberglass.

34. The article of claim 31 wherein the substrate is a vessel hull.

35. The article of claim 31, wherein the nutritional source is present in the degradable material or an additive to the degradable material.

36. A method of preventing fouling comprising the steps of:
providing a bio-supportive medium; and
applying the bio-supportive medium to a substrate;
the bio-supportive medium comprising:

a degradable material;

at least one nutritional source; and at least one bio-limiting agent dispersed in the degradable material;

wherein the degradable material, the at least one nutritional source, and the at least one bio-limiting agent are provided in quantities, such that the bio-supportive medium is capable of supporting formation of a biomass having at least a specific consortium of organisms of identical or different species, substantially at equilibrium within its environment or host habitat; wherein the at least one nutritional source and the at least one bio-limiting agent are selected to control the amount and type of species present in the biomass.

37. The method of claim 36, wherein the degradable material comprises at least one epoxy resin.

38. The method of claim 36, wherein the nutritional source is present in the degradable material or an additive to the degradable material.

* * * * *